US007902158B2

(12) United States Patent
Kuszmann et al.

(10) Patent No.: US 7,902,158 B2
(45) Date of Patent: Mar. 8, 2011

(54) POLYSULFATED GLYCOSIDES AND SALTS THEREOF

(75) Inventors: János Kuszmann, Budapest (HU); István Kurucz, Budapest (HU); Gábor Medgyes, Budapest (HU); Nicholas Bodor, Bal Harbour, FL (US)

(73) Assignee: Ivax Drug Research Ltd. (HU)

( * ) Notice: Subject to any disclaimer, the term of this patent is extended or adjusted under 35 U.S.C. 154(b) by 34 days.

(21) Appl. No.: 11/659,406

(22) PCT Filed: Aug. 5, 2005

(86) PCT No.: PCT/US2005/027877
§ 371 (c)(1),
(2), (4) Date: Jul. 25, 2007

(87) PCT Pub. No.: WO2006/017726
PCT Pub. Date: Feb. 16, 2006

(65) Prior Publication Data
US 2007/0281893 A1 Dec. 6, 2007

Related U.S. Application Data

(60) Provisional application No. 60/599,148, filed on Aug. 5, 2004.

(51) Int. Cl.
*A01N 43/04* (2006.01)
*A61K 31/70* (2006.01)
*A61K 31/715* (2006.01)
(52) U.S. Cl. ............................................. 514/25; 53/826
(58) Field of Classification Search .................... 514/25, 514/53, 826
See application file for complete search history.

(56) References Cited

U.S. PATENT DOCUMENTS 5,403,927 A 4/1995 Bendiak
5,783,568 A * 7/1998 Schlessinger et al. .......... 514/53

FOREIGN PATENT DOCUMENTS

| EP | 0529715 | | 3/1993 |
| EP | 0771815 | | 5/1997 |
| JP | 2000256385 | | 9/2000 |
| WO | WO 89/05646 | * | 6/1989 |
| WO | WO-94/14849 A1 | | 7/1994 |
| WO | WO-95/34313 A1 | | 12/1995 |
| WO | WO 02/083700 | * | 10/2002 |
| WO | WO-03/1044733 A2 | | 12/2003 |

OTHER PUBLICATIONS

Definition of "isomers" from the American Heritage Dictionary [online], [Retrieved on Oct. 6, 2009]. Retrieved from the internet <http://dictionary.reference.com/search?q=isomers&r=66>.*
Hodgson, J.L. and Hodgson, D.R. (2002) Inflammatory Airway Disease in Equine Respiratory Diseases. Edited by P. Lekeux. Published by International Veterinary Information Service, Ithaca, New York.*
Redington, A.E., Roche, W.R., Madden, J., Frew, A.J., Djukanovic, R., Holgate, S.T., Howarth, P.H. (2001) Basic fibroblast growth factor in asthma: Measurement in bronchoalveolar lavage fluid basally and following allergen challenge. Journal of Allergy and Clinical Immunology, vol. 107, No. 2, p. 384-387.*
Li, X., Wilson, J.W. (1997) Increased Vascularity of the Bronchial Mucosa in Mild Asthma. American Journal of Respiratory and Critical Care Medicine, vol. 156, p. 229-233.*
Search Report from correspoding Singapore Application No. 200700408.8.
French et al., "Constitution of stachyose", Journal of the American Chemical Society, vol. 75, pp. 3664-3666, 1953.
Takeo et al., "Partial benzoylation of methyl .beta.-kojiboside and methyl .beta.-sophoroside", Carbohydrate Research, vol. 86, pp. 297-330, 1980.
Torgov et al., "Structural studies of the O-specific polysaccharide from *Salmonella* kentucky strain 98/3 (0:8, H:i,Z6)", Carbohydrate Research, vol. 208, pp. 293-300, 1990.
Nelson et al., "Separation and characterization of the soluble and insoluble components of insoluble laminaran", Carbohydrate Research, vol. 33, pp. 63-74, 1974.
Goldstein et al., "The synthesis and characterization of 4-0-(.alpha., D-glucopyransoyl)-6-0- (.beta.-D-glyucopyransol)-D-glucose", ACTA Chemica Scandinavica, vol. 16, pp. 383-386, 1962.
Bailey et al., Immunopolysaccharides. IX. The enzymic syntheses of trisaccharides containing the .alpha.-1,2-glucosidic linkage, Journal of the Chemical Society, pp. 1895-1902, 1958.

* cited by examiner

*Primary Examiner* — Shaojia Anna Jiang
*Assistant Examiner* — Scarlett Goon
(74) *Attorney, Agent, or Firm* — Lerner, David, Littenberg, Krumholz & Mentlik, LLP

(57) ABSTRACT

The invention relates to polysulfated glycosides of formula (I), the pharmaceutically acceptable salts thereof, as well as the pharmaceutical compositions containing these compounds as active ingredients. Furthermore the invention provides a method of preventing, treating or alleviating the symptoms of acute and chronic inflammatory disorders of the airways of mammals—including asthma and asthma-related pathologies.

17 Claims, No Drawings

POLYSULFATED GLYCOSIDES AND SALTS THEREOF

CROSS REFERENCE TO RELATED APPLICATIONS

The present application is a national phase entry under 35 U.S.C. §371 of International Application No. PCT/US2005/027877, filed Aug. 5, 2005, published in English, which claims benefit of U.S. Provisional Patent Application No. 60/599,148, filed Aug. 5, 2004. The disclosures of all of said applications are incorporated by reference herein.

BACKGROUND OF THE INVENTION

1. Field of the Invention

The present invention relates to glycosides, the salts thereof and pharmaceutical compositions containing these glycosides as active ingredients. Furthermore the invention provides a method of preventing, treating or alleviating the symptoms of acute and chronic inflammatory disorders of the airways of mammals—including asthma and asthma-related pathologies.

2. Summary of Related Art

Inflammation is a multi-step cascade process, any part of which may be the subject of potential therapeutic intervention. Briefly, inflammation entails the infiltration of immunologically competent cells (for example eosinophils, mast cells, activated T-lymphocytes) into the injury site where they, together with resident cells, release bioactive mediator substances (e.g., histamine, proteases, a host of cytokines and chemokines), which increase the permeability of nearby blood vessels, attract and stimulate bystander cells. The altered permeability of vessels results in a fluid exudate forming at the injury site followed by a further influx of reactive leukocytes and their eventual efflux into the damaged area (For an overview see, Trowbridge and Emling, *Inflammation: A Review of the Process* Quintessence Pub. Co., 1997). Secretion of collagen and mucus by, and proliferation of, resident cells (smooth muscle and epithelial cells or fibroblasts stimulated by the released mediators) establish the extension of pathological alterations (e.g., airway obstruction) and contribute to their development.

Inflammation is associated with a variety of pulmonary conditions including e.g., intrinsic or extrinsic asthma bronchiale, any inflammatory lung disease, acute or chronic bronchitis, pulmonary inflammatory reactions secondary to chronic bronchitis, chronic obstructive lung disease, pulmonary fibrosis, as well as any pulmonary condition in which white blood cells may play a role including, but not limited to, idiopathic pulmonary fibrosis and any other autoimmune lung disease. Asthma is one of the most common forms of pulmonary inflammation affecting the large and small airways of the lung. It impacts on 5% to 10% of the human population, resulting in an estimated 27 million patient visits, 6 million lost workdays, and 90.5 million days of restricted activity per year. The morbidity and mortality rates for asthma are growing worldwide (Plaut and Zimmerman, "Allergy and Mechanisms of Hypersensitivity" in *Fundamental Immunology, 3rd* Ed., Paul (ed.), Raven Press, New York N.Y., at 1399 (1993)).

Conventional anti-asthma treatments have been predicated on the strict avoidance of all triggering allergens, which is inherently difficult to achieve, and on therapeutic regimens based on pharmacological agents having unfortunate side effects and suboptimal pharmacokinetic properties. $\beta_2$-adrenergic agonists used to treat bronchospasm have no effect on airway inflammation or bronchial hyperreactivity (Palmer et al., *New Engl. J. Med.* 331:1314 (1994)). Also, regular or prolonged use of $\beta_2$-adrenergic agonists is associated with poor control of asthma, increase in airway hyperresponsiveness to allergen, and reduced bronchoconstriction protection (Bhagat et al., *Chest* 108:1235 (1995)). Moreover, chronic use of $\beta_2$-adrenergic agents alone, by causing down regulation of $\beta_2$-adrenergic receptors, is suspected to worsen bronchial hyperreactivity. Theophylline (an anti-asthma methylxanthine) is characterized by substantial variability in its absorbance and clearance. Corticosteroids, while relatively safe in adult patients, are toxic for children, resulting in adrenal suppression and reduced bone density and growth (Woolock et al., *am. Respir. Crit. Care Med.* 153:1481 (1996)). Cromolyn, used to prevent asthmatic episodes, is effective in preventing an asthmatic reaction only if given prior to an attack (Volcheck et al., *Postgrad Med.* 104(3):127 (1998)). Antihistamines occasionally prevent or abort allergic asthmatic episodes, particularly in children, but often are only partially effective because histamines are only one of many inflammation associated mediators (Cuss, "The Pharmacology of Antiasthma Medications", in *Asthma as an Inflammatory Disease*, O'Byrne, Ed., Dekker, Inc., New York, at 199 (1990)) and O'Byrne, "Airway Inflammation and Asthma", in *Asthma as an Inflammatory Disease*. O'Byrne, Ed., Dekker, Inc., New York, N.Y., 143 (1990)).

Thus, current drug modalities suffer from a number of drawbacks. In general conventional agents have a relatively short duration of action and may be partially or wholly in effective when administered after antigen challenge occurs. Moreover, because of serious adverse effects associated with the use of agents such as $\beta_2$-adrenergic agonists and corticosteroids, therapeutic margins of safety with such agents are relatively narrow and patients using such agents must be carefully monitored (see e.g., WO 94/06783, WO 99/06025, U.S. Pat. Nos. 5,690,910 and 5,980,865). In a recent clinical study, of inhaled corticosteroids, only transient improvement occurred in the airways function of 5-11-year-old asthmatic children after the first year of therapy, with regression to that observed with placebo over the next 3 years (The Childhood Asthma Management Program Research Group, *N Engl. J. Med*, 343:1054 (2000)). This regression can best be explained by remodeling changes (characteristic feature of asthma) occurring in the airways that are refractory to corticosteroids (Davies, *Curr. Opin. Allergy Clin. Immunol.*, 1:67 (2001)).

It is known from relevant literature, that certain mixtures of polysulfated disaccharides—having structures closely related to those of the present invention and which were synthesized by nitrous acid treatment of such natural products as for example heparin or heparin sulfate, followed by reduction with borohydride and subsequent sulfation of the partially purified samples (U.S. Pat. No. 5,690,910; 5,980,865 and WO 02/083700)—displayed remarkable anti-inflammatory effect in different asthma models.

SUMMARY OF THE INVENTION

The present invention relates to novel glycosides and processes to make such compounds and pharmaceutical compositions containing such compounds, with well-defined chemical structures, which have more favourable pharmacological properties and less undesirable side-effects, than the known anti-asthmatics. The invention further relates to methods of treating patients in need of treatment comprising administering the novel glycosides and compositions of said glycosides to said patients.

DETAILED DESCRIPTION OF THE INVENTION

According to the facts mentioned above the invention relates to novel polysulfated glycosides of formula (I),

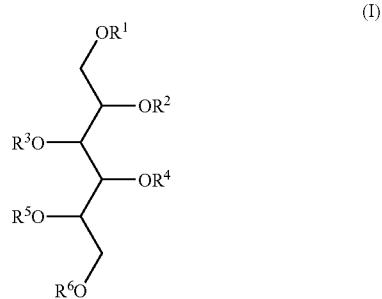

(I)

wherein $R^1$, $R^2$, $R^3$, $R^4$, $R^5$ and $R^6$ independently of each other, stand for —H, $C_{1-4}$ alkyl, —$SO_3H$, sulfated or unsulfated glycosyl or sulfated or unsulfated or unsulfated diglycosyl group—with the proviso, that at least one of $R^1$-$R^6$ is a sulfated or unsulfated glycosyl or sulfated or unsulfated diglycosyl group—as well as the possible isomers and pharmaceutically acceptable salts thereof. The term "pharmaceutically acceptable salts" includes, for example, alkali salts and alkaline earth metal salts and any other pharmaceutically acceptable counterion or counterions associated with one or more of the sulfate groups on the modecule.

As all of the four secondary carbon atoms of the sugar alcohol represent chiral centers, obviously all possible stereoisomers (allitol, galactitol, iditol, mannitol, glucitol and talitol) as well as the D- and L-enantiomers thereof are covered by formula (I). The term "isomer" herein includes all such compounds and variants thereof in the compound of formula (I)

The meaning of sulfated glycosyl group can be any pentopyranose or hexopyranose molecule with optional configuration, one or more of the hydroxyl groups of which are present as an O-sulfate ester and the sugar moiety is attached to the aglycon with its anomeric carbon atom via an α- or β-linkage. The unsulfated glycosyl group contains all hydroxyl groups or protected versions thereof. The unsulfated compounds are useful as intermediates to produce the sulfated compounds recited herein.

The meaning of polysulfated diglycosyl group can be any pentopyranose or hexopyranose molecule with optional configuration, one of the hydroxyl group of which is glycosylated with a further pentopyranose or hexopyranose molecule with optional configuration, and all of the hydroxyl groups of the so formed diglycosyl unit are present as O-sulfate esters and the sugar moiety is attached to the aglycon with its anomeric carbon via α- or β-linkage.

All possible stereoisomers (arabino-, Zyxo-, ribo- and xylo-) are included in the structure of pentoses, as well as D- and L-enantiomers thereof. Similarly all possible stereoisomers (allo-, altro-, galacto-, gluco-, gulo-, ido-, manno- and tallo-) are included in the structure of hexoses, as well as D and L-enantiomers thereof. The term "isomer" includes all such compounds and variations thereof in the compound at formula (1).

The meaning of $C_{1-4}$ alkyl group, is a methyl, ethyl, n-propyl, isopropyl, n-butyl, isobutyl, sec-butyl, tert-butyl group, preferably methyl group.

Alkali metal salts of the compounds of the invention mean. Na, K or Li salts, while alkaline-earth metal salts preferably are Mg and Ca salts.

Those compounds of formula (I), as well as alkali metal and alkaline-earth metal salts thereof, wherein the meaning of $R^1$ is a polysulfated glycosyl or diglycosyl group and the meaning of $R^2$-$R^6$ is —$SO_3H$, represent a preferred group of the compounds of the invention.

Those compounds of formula (I), as well as alkali metal and alkaline-earth metal salts thereof, wherein the meaning of $R^1$, $R^2$, $R^3$, $R^4$ $R^5$ and $R^6$ is —$SO_3H$ and the meaning of $R^3$ is a polysulfated glycosyl or diglycosyl group, represent a further preferred group of the compounds of the invention.

Those compounds of formula (I), as well as alkali metal and alkaline-earth metal salts thereof, wherein the meaning of $R^1$, $R^2$, $R^3$, $R^4$, $R^5$ and $R^6$ is —$SO_3H$ and the meaning of $R^4$ is a polysulfated glycosyl or diglycosyl group, represent a further preferred group of the compounds of the invention.

Those compounds of formula (I), as well as alkali metal and alkaline-earth metal salts thereof, wherein the meaning of $R^1$ and $R^6$ is a polysulfated glycosyl group and the meaning of $R^2$, $R^4$, $R^5$ and $R^2$ is —$SO_3H$, represent a further preferred group of the compounds of the invention.

Those compounds of formula (I), as well as alkali metal and alkaline metal salts thereof, wherein the meaning of $R^1$ and $R^6$ is a polysulfated glycosyl or diglycosyl group and the meaning of $R^2$, $R^3$, $R^4$ and $R^5$ is —$SO_3H$, represent a further preferred group of the compounds of the invention.

Those compounds of formula (I), as well as alkali metal and alkaline-earth metal salts thereof, wherein the meaning of $R^1$ is a polysulfated glycosyl or diglycosyl group, the meaning of $R^3$ and $R^4$ is a $C_{1-4}$ alkyl group, while the meaning of $R^2$, $R^5$ and $R^6$ is —$SO_3H$, represent a further preferred group of the compounds of the invention.

Those compounds of formula (I), as well as alkali metal and alkaline earth metal salts thereof, wherein the meaning of $R^1$ and $R^6$ is a polysulfated glycosyl or diglycosyl group, the meaning of $R^3$ and $R^4$ is a $C_{1-4}$ alkyl group, while the meaning of le and $R^5$ is —$SO_3H$, represent a further preferred group of the compounds of the invention.

Especially preferred representatives of the compounds of formula (I) of the present invention are—without limitation—the following:

2,3,4,5,6-penta-O-sulfato-1-O-sulfato-2,3,4,6-tetra-O-sulfato-β-D-glucopyranosyl)-D-mannitol nona potassium salt, 1,2,3,4,5-penta-O-sulfato-6-O-2,3,4,6-tetra-O-sulfato-β-D-glucopyranosyl)-D-glucitol nona potassium salt, 2,3,4,5,6-penta-O-sulfato-1-O-(2,3,4,6-tetra-O-sulfato-β-D-glucopyranosyl)-D-glucitol nona potassium salt, 1,2,4,5,6-penta-O-sulfato-3-O-(2,3,4,6-tetra-O-sulfato-β-D-glucopyranosyl)-D-glucitol nona potassium salt, 1,2,3,5,6-penta-O-sulfato-4-O-(2,3,4,6-tetra-O-sulfato-β-D-glucopyranosyl)-D-glucitol nona potassium salt, 1,2,3,5,6-penta-O-sulfato-4-O-(2,3,4,6-tetra-O-sulfato-β-D-glucopyranosyl)-D-glucitol nona potassium salt, 1,2,3,5,6-penta-O-sulfato-4-O-(2,3,4,6-tetra-O-sulfato-β-D-galactopyranosyl)-D-glucitol nona potassium salt, 2,4,5,6-tetra-O-sulfato-1,3-bis-O-(2,3,4,6-tetra-O-sulfato-β-D-glucopyranosyl)-D-glucitol dodeca potassium salt, 2,4,5,6-tetra-O-sulfato-1,6-bis-O-(2,3,4,6-tetra-O-sulfato-β-D-glucopyranosyl)-D-mannitol dodeca potassium salt, 2,4,5,6-tetra-O-sulfato-1,6-bis-O-2,3,4,2',3',4',6'-hepta-O-sulfato-β-gentiobiopyranosyl)-D-mannitol octadeca potassium salt, 2,3,4,5,6-penta-O-sulfato-1-O-(2,3,4,2',3',4',6'-hepta-O-sulfato-β-gentiobiopyranosyl)-D-mannitol dodeca potassium salt, 3,4-di-O-methyl-2,5,6-tri-O-sulfato-1-O-(2,3,4,6-tetra-O-sulfato-β-D-glucopyranosyl)-D-mannitol hepta potassium salt, 3,4-di-O-methyl-2,5-di-O-sulfato-1,6-bis-O-(2,3,4,6-tetra-O-sulfato-β-D-glucopyranosyl-D-mannitol deca potassium salt, 3,4-di-O-methyl-2,5,6-tri-O-sulfato-1-O-(2,3,4,2',3',4',6'-hepta-O-sulfato-β-gentiobiopyranosyl)-D-mannitol deca potassium salt, 3,4-di-O-methyl-2,5-di-O-sulfato-1,6-bis-O-(2,3,6,2',3',4',6'-hepta-O-sulfato-β-lactosyl)-D-mannitol hexadeca potassium salt, 2,3,4,5,6-penta-O-sulfato-1-O-2,3,4-tri-O-sulfato-α-D-arabinopyranosyl)-D-mannitol octa potassium salt, 2,3,4,5,6-penta-O-sulfato-1-O-(2,3,4-tri-O-sulfato-β-D-xylopyranosyl)-D-mannitol potassium salt, 2,4,5,6-tetra-O-sulfato-1,6-bis-O-(2,3,4,6-tetra-O-sulfa-β-D-glucopyranosyl)-galactitol dodeca potassium salt, 1,2,4,5,6-penta-O-sulfato-3-O-(2,3,4,6-tetra-O-sulfato-β-D-glucopyranosyl)-D-glucitol nona sodium salt.

Compounds of formula (I) of the present invention can be synthesized from compounds of formula (II)

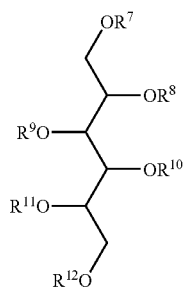

(II)

wherein $R^7$, $R^8$, $R^9$, $R^{10}$, $R^{11}$ and $R^{12}$ independently of each other, stand for hydrogen atom, $C_{1-4}$ alkyl, glycosyl or diglycosyl group, and at least one of $R^7$-$R^{12}$ is a glycosyl or diglycosyl group—by transforming its free hydroxyl groups into sulfate esters using known methods.

Sulfur trioxide or an adduct thereof formed with an organic base (for example triethylamine or pyridine) or with dimethylformamide can be used as reagent for the preparation of O-sulfate esters.

Optionally monofunctional acidic esters obtained by the above methods can be transformed into salts for example with alkali metal or alkali earth-metal acetates. After purification, salts can be obtained by freeze drying, precipitation or crystallization.

Some of the compounds of formula (I), used as starting materials in the above process for the synthesis of compounds of formula (I) of the present invention can be synthesized for example by the following, known methods:

Those compounds of formula (II), wherein one from among $R^7$ and $R^8$ represents a glycosyl group and the other represents hydrogen atom, as well as the meaning of $R^9$-$R^{12}$ is hydrogen atom, can be synthesized for example by using a compound of formula (In) or (IV)

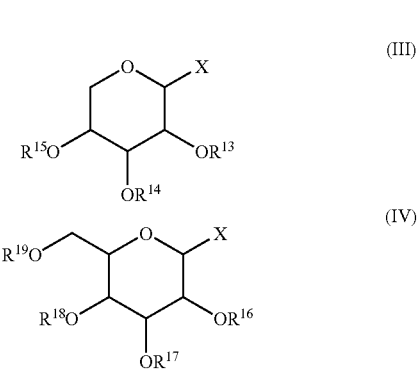

wherein X stands for a halogen atom, trichloroacetimidate or phenylthio group and $R^{13}$-$R^{19}$ represent an aliphatic or aromatic ester or an ether group—as donor molecule and a compound of formula (V),

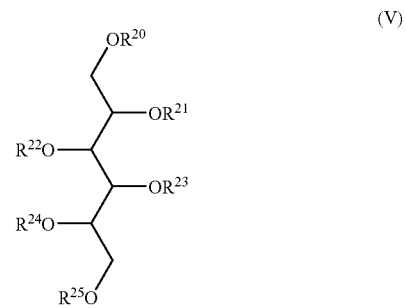

wherein $R^{20}$ and $R^{21}$ stand for hydrogen atom, $R^{22}$-$R^{25}$ represent ether type protective groups, as acceptor and the glycosylation is carried out in the presence of appropriate activators. Then the protective groups are cleaved from the so obtained compound of formula (V)—wherein $R^{22}$-$R^{25}$ stand for an ether type protective group, while one of $R^{20}$ and $R^{21}$ represents a protected glycosyl group and the other is hydrogen atom.

According to another process a compound of formula (V) is used as acceptor in the above reaction, in which $R^{20}$ and $R^{22}$ stand for hydrogen atom, while $R^{21}$, $R^{23}$, $R^{24}$ and $R^{25}$ represent ether type protective groups, then the protective groups are cleaved from the so obtained compound of formula (V)—wherein $R^{21}$, $R^{23}$, $R^{24}$ and $R^{25}$ are ether type protective groups, $R^{20}$ represents a protected glycosyl group and $R^{22}$ is hydrogen atom.

Those compounds of formula (II), wherein $R^7$ and $R^9$ stand for a glycosyl group, while $R^9$, $R^{10}$, $R^{11}$ and $R^{12}$ represent hydrogen atom, can be synthesized for example by carrying out the glycosylation according to process b) but using the donor molecule in excess and the protective groups are cleaved from the so obtained compound of the general formula (V)—wherein $R^{20}$ and $R^{22}$ represent protected glycosyl groups and $R^{21}$, $R^{23}$, $R^{24}$ and $R^{25}$ are ether type protective groups.

Those compounds of formula (II), wherein one from among $R^7$ and $R^8$ represents a diglycosyl group, the other is hydrogen atom, and $R^9$-$R^{12}$ stand for hydrogen atom, can be synthesized for example by using a compound of formula (VI) or (VII)

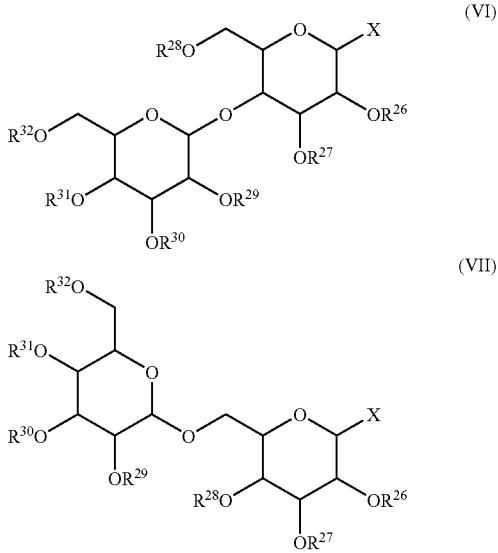

wherein X stand for a halogen atom, trichloroacetimidate or phenylthio group and $R^{26}$-$R^{32}$ represent an aliphatic or aromatic ester or ether group—as donor molecule and a compound of formula (V), wherein $R^{20}$ and $R^{21}$ stand for hydrogen atom, $R^{22}$-$R^{25}$ represent ether type protective groups, as acceptor and the glycosylation is carried out in the presence of appropriate activators. Then the protective groups are cleaved from the so obtained compound of the general formula (V)—wherein $R^{22}$-$R^{25}$ are ether type protective groups, while one from among $R^{20}$ and $R^{21}$ represents a protected glycosyl group and the other is hydrogen atom.

Those compounds of formula (II), wherein $R^7$ stands for a diglycosyl group, can be synthesized for example by using a compound of formula (V), wherein $R^{20}$ and $R^{25}$ are hydrogen atom, $R^{21}$ and $R^{24}$ represent ester type protective groups, while $R^{22}$ and $R^{23}$ are ether type protective groups, as acceptor in the above reaction, then the protective groups are cleaved from the so obtained compound of formula (V)—wherein $R^{21}$ and $R^{24}$ represent ester type protective groups, while $R^{22}$ and $R^{23}$ are ether type protective groups, $R^{20}$ represents a protected diglycosyl group and the meaning of $R^{25}$ is hydrogen atom.

Those compounds of formula (II), wherein $R^7$ and $R^{12}$ stand for a diglycosyl group, and $R^8$-$R^{11}$ represent hydrogen atom, can be synthesized for example by using a compound of formula (VI) or (VI),—wherein X stands for a halogen atom, trichloroacetimidate or phenylthio group and $R^{26}$-$R^{32}$ represent aliphatic or aromatic ester or ether groups—as donor molecule in excess and a compound of formula (V), wherein $R^{20}$ and $R^{25}$ stand for hydrogen atom, $R^{21}$ and $R^{24}$ represent ester type protective groups, while $R^{22}$ and $R^{23}$ are ether type protective groups, as acceptor and the glycosylation is carried out in the presence of appropriate activators. Then the protective groups are cleaved from the so obtained compound of formula (V)—wherein $R^{21}$ and $R^{24}$ are ester type protective groups, $R^{22}$ and $R^{23}$ represent ether type protective groups, while $R^{20}$ and $R^{25}$ are protected diglycosyl groups.

In the above glycosylation reactions mercury or silver salts, boron trifluoride diethyl etherate, N-iodosuccinimide and trifluoromethanesulfonic acid or the mixture of the latter two can be used as activator.

The cleavage of the protective groups can be carried out by acid hydrolysis or reduction in the presence of a catalyst in the case of ethers and acetals, while in the case of esters Zemplin's method (base catalysed trans-esterification) or hydrolysis in the presence of a base can be used.

Abbreviations and Expressions Used in the Description:
Ac=acetyl
Bz=benzoyl
Me=methyl
Ph=phenyl
NIS=N-iodosuccinimide
TfOH=trifluoromethanesulfonic acid As used in this specification, the singular forms "a", "an" and "the" specifically also encompass the plural forms of the terms to which they refer, unless the content clearly dictates otherwise. For example, reference to "a modulator" includes mixtures of modulators.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or."

As used herein, the terms "treating" or "treatment" are used to indicate reducing, alleviating, preventing, inhibiting the development of and/or reversing the symptoms of a condition. Conditions to be treated by the methods and compositions of the invention include any condition characterized by, or including, acute and chronic inflammatory disorders of the airways. Hence, the terms "inflammatory disorder" or "inflammatory disorders of the airways" encompass any inflammatory lung disease, including asthma, intrinsic or extrinsic asthma bronchiale, acute chronic bronchitis, allergic rhinitis, pulmonary inflammatory and structural reactions secondary to chronic bronchitis, chronic obstructive lung disease, pulmonary fibrosis. The invention is also useful for pulmonary condition in which white blood cells and airway remodeling may play a role including but not limited to idiopathic pulmonary fibrosis and any other autoimmune lung disease.

By "asthma" is meant a condition of allergic origins, the symptoms of which include continuous or paroxysmal labored breathing accompanied by wheezing, a sense of constriction in the chest, and often attacks of coughing or gasping. By "asthma-related pathology" is meant a condition whose symptoms are predominantly inflammatory in nature with associated bronchospasm. Hence, both asthma and asthma-related pathologies are characterized by symptoms that include narrowing of airways, due in varying degrees to contraction (spasm) of smooth muscle, edema of the mucosa, including that of the upper airways and mucus in the lumen of the bronchi and bronchioles. Non-limiting representative examples of "asthma-related pathologies" include non-asthmatic conditions characterized by airway hyperresponsiveness (e.g., chronic bronchitis, emphysema, cystic fibrosis and respiratory distress).

Compositions and methods taught herein are exemplified, for asthma. However, the invention should not be construed as limited to this particular pulmonary disease. Asthma offers the advantage of having been studied extensively and provides several accepted models to evaluate the invention. It is known that sensitization and allergen challenge leads to airway hyperresponsiveness to various agonists. Hence, acetylcholine, known as a spasmogenic agent, is capable of inducing larger contractions of the muscle cells in tissues obtained from the trachea of sacrificed animals (which had been sensitized to provoke airway hyper-responsiveness) than from control animals following allergen challenge (see, e.g. Tokuoka et al., *Br. J. Pharmacol.* 134:1580 (2001); Nakata et al., *Int. Immunol.* 13:329 (2001); Emala and Hirshman, *Monogr. Allergy* 33:35 (1996)).

The most prominent characteristic of asthma is bronchospasm, or narrowing of the airways. Asthmatic patients have prominent contraction of the smooth muscles of large and small airways, increased mucus production, and increased inflammation (Plaut and Zimmerman, supra). The inflammatory response in asthma is typical for tissues covered by a mucosa and is characterized by vasodilation, plasma exudation, recruitment of inflammatory cells such as neutrophils, monocytes, macrophages, lymphocytes, and eosinophils to the sites of inflammation, and the release of inflammatory mediators by resident tissue cells (e.g., mast cells or airways epithelial cells) or by migrating inflammatory cells (Hogg, "Pathology of Asthma", in *Asthma as an Inflammatory Disease*, O'Byrne (ed.), Marcel Dekker, Inc., New York, N.Y., at 1 (1990)). Asthma may be triggered by a variety of causes such as allergic reactions, a secondary response to infections, industrial or occupational exposures, ingestion of certain chemicals or drugs, exercise (Hargreave et al., *J. Allergy Clin. Immunol.* 83:1013 (1986)).

The compounds of formula (I) according to the invention have also been found effective to decrease mucus production of bronchial epithelial cells and to inhibit growth factor mediated proliferation of smooth muscle cells.

An increase in bronchial hyperreactivity (AHR), the hallmark of a more severe form of asthma, can be induced by both airway antigenic and non-antigenic stimuli. Late phase response and persistent hyperresponsiveness in allergen-induced asthma have been associated with the recruitment of leukocytes, and particularly eosinophils, to inflamed lung tissue (Abraham et al., *Am. Rev. Respir. Dis.* 138:1565 (1988)). Eosinophils release several inflammatory mediators including 15-HETE, leukotriene C4, PAF, cationic proteins, eosinophil peroxidase.

The terms "antigen" and "allergen" are used interchangeably to describe those molecules, such as dust or pollen that can induce an allergic reaction and/or induce asthmatic symptoms in an individual suffering from asthma. Thus, an asthmatic individual "challenged" with an allergen or an antigen is exposed to a sufficient amount of the allergen or antigen to induce an asthmatic response. The compounds of formula (I) according to the invention have been found effective to treat AHR subsequent to ovalbumin sensitization and antigen challenge.

The biological activity of the compounds of formula (I) of the present invention in different animal models is demonstrated below:

Model 1

Examination of the Effect of Locally Administered Polysulfated Glycosides on Airways Hyper-Responsiveness Ex Vivo Inflammation of the airways may lead to bronchial hyperresponsiveness, which is a characteristic feature of asthma Brown Norway (EN) rats were actively sensitized to ovalbumin (OA) by a subcutaneous injection of 0.5 ml of OA/Al(OH)$_3$ gel mixture (2 mg OA+10 g Al(OH)$_3$/100 ml saline) on day 0.1 with subsequent subcutaneous injections (10 mg OA+10 g Al(OH)$_3$/100 ml saline) given on days 14 and 21. On day 28, animals received the compound described in example 4 intratracheally (0.01; 0.1 or 1.0 mg/kg dose) 2 hours before antigen challenge. Antigen challenge was performed by inhalation of nebulised ovalbumin (1% antigen solution administered in a TSE inhalation system for 1 hour). Animals were sacrificed 48 hours post antigen challenge wherein the tracheas were removed to an organ bath. Dissected tracheas were allowed to equilibrate for 30 minutes before measuring tracheal spasmogenic response curves to acetylcholine (Ach).

As shown in Table 1 ovalbumin challenge of sensitized animals in this model caused a significant tracheal hyperreactivity to acetylcholine, when the response to the spasmogenic agent was determined 48 h after antigen challenge. The compound described in example 4 in a dose of 0.01 mg/kg, brought this elevation back almost to control level.

TABLE 1

Effect of antigen challenge and intratracheal pretreatment with compound of Example 4 on the tracheal contraction to acetylcholine in BN-rate

| Parameters | Control | Placebo | Examined compound | |
| --- | --- | --- | --- | --- |
|  |  |  | 0.01 mg/kg | 1.0 mg/kg |
| ED$_{50}$* | 4.73 ± 0.05 | 5.51 ± 0.21 | 4.40 ± 0.30 | 4.60 ± 0.55 |
| p | 0.032 |  | <0.05 | <0.05 |
| MAX** | 100 ± 0 | 334 ± 68 | 134 ± 26 | 116 ± 37 |
| p | 0.006 |  | <0.05 | <0.05 |

*log M acetylcholine (Ach), causing 50% contraction relative to control (mean ± SEM)
**Contraction at maximal Ach concentration relative to control (mean ± SEM)

Model 2.

Examination of the Effect of Polysulfated Glycosides on the Allergen Stimulated Mucus Production of Airways Epithelial Cells.

In a sensitized animal antigenic challenge results in mucus production of airways epithelial cells, which is a characteristic feature of allergic asthma Sensitized BN rats were treated intratracheally with varying (0.01-1.0 mg/kg) dose of compound described in example 4, two hours before antigenic challenge, using a similar protocol described in Model 1. Lungs were collected 48 hours after challenge and were fixed in 8% phosphate buffered formaldehyde. Samples were then processed for histochemistry routinely. 5 μm thick sections were stained with periodic-acid-Schiff (PAS) reagents and were counterstained with haematoxylin-eosine. On the sections each epithelial cells of the airways were counted in the whole preparation at a magnification of 400×. The number of PAS(+) [mucus producing] epithelial cells was expressed as the ratio of the total number of epithelial cells.

As it is shown in Table 2, allergen challenge stimulates the mucus production of airways epithelial cells (control vs. challenge). The compound significantly decreased the number of PAS(+), mucus producing cells at the applied higher dose.

TABLE 2

Effect of antigen challenge and intratracheal treatment with compound of Example 4, on the allergen induced mucus production of airways epithelial cells in BN rats

| Groups | Dose mg/kg | %* | p-value |
|---|---|---|---|
| Control | | 2.2 ± 0.9 | <0.001 |
| Challenge | | 15.8 ± 2.8 | — |
| Treated | 0.01 mg/kg | 15.0 ± 2.7 | NS |
| | 0.1 mg/kg | 6.3 ± 1.5 | <0.001 |

*number of PAS(+) cells as percent of total number of cells (average ± SEM)

Model 3.
Examination of the Effect of Polysulfated Glycosides on the Extent of Perivascular Oedema Developed in Asthmatic Lung Tissue.

In a sensitized animal antigen challenge, as a result of the developing inflammatory processes, increases the permeability of the blood vessels resulting in plasma excudation around the periphery of the vasculature.

Sensitized BN rats were treated intratracheally with varying (0.01-1.0 mg/kg) dose of compound described in example 4, two hours before antigenic challenge, using a similar protocol described in Model 1. Lungs were collected 48 hours after challenge and were fixed in 8% phosphate buffered formaldehyde. Samples were then processed for histochemistry routinely. 5 μm thick sections were stained with periodic-acid-Schiff (PAS) reagents and were counterstained with haematoxylin-eosine. On the 5 μm sections, the area of the connective tissue around the vasculare was determined and expressed as a ratio of the area of the corresponding blood vessel itself.

As it is shown in Table 3, allergen challenge causes aedema around the vasculature, the extent of which was significantly decreased even at the smallest dose of the examined compound.

TABLE 3

Effect of antigenic challenge and intratracheal treatment with compound of Example 4, on the extent of developing oedema in BN rats

| Groups | Dose mg/kg | Oedema* | p-value |
|---|---|---|---|
| Control | | 55 ± 6 | <0.001 |
| Challenge | | 209 ± 12 | — |
| Treated | 0.01 mg/kg | 113 ± 7 | <0.001 |
| | 0.1 mg/kg | 106 ± 8 | <0.001 |

*area of oedema relative to area of vasculature (average ± SEM)

Model 4.
IP-3 Receptor Antagonistic Effect of Polysulfated Glycosides

Glycosides of the present invention, depending on their chemical stir, inhibit the binding of inositol-1,4,5-trisphosphate (IP3) to its receptor in microsomal membrane preparations. As IP3 is a messenger molecule playing distinguished role in the activation of different cells, interfering with this function can explain the anti-asthmatic effect of these polysulfated glycosides.

The IP3 antagonist effect of the polysulfated glycosides were determined using rat cerebellum membrane preparations according to Worley et al. (JBC 262, 12132, 1987). As is shown in Table 4, all the compounds described in Examples 1-16 possess varying IP3 antagonist activity.

TABLE 4

IP-3 receptor antagonistic effect of polysulfated glycosides

| Compound (Number of example) | $IC_{50}$ (μg/ml) Average ± SEM (n) | Average $IC_{50}$ (nM) |
|---|---|---|
| 1 | 0.14 ± 0.03 (4) | 100 |
| 2 | 1.99 ± 0.51 (3) | 1413 |
| 3 | 0.57 ± 0.12 (3) | 405 |
| 4 | 0.23 ± 0.06 (4) | 163 |
| 5 | 0.37 ± 0.18 (4) | 263 |
| 6 | 0.36 ± 0.10 (5) | 256 |
| 7 | 0.36 ± 0.07 (3) | 256 |
| 8 | 1.54 ± 0.21 (3) | 800 |
| 9 | 1.22 ± 0.14 (3) | 634 |
| 10 | 0.87 ± 0.36 (4) | 284 |
| 14 | 10.46 ± 2.28 (6) | 6095 |
| 16 | 1.93 ± 0.08 (3) | 702 |

The pharmaceutical compositions of the present invention are intended for use with any mammal that may experience the benefits of the methods of the invention. Foremost among such mammals are humans, although the invention is not intended to be so limited, and is applicable to veterinary uses, in accordance with the invention, "mammal" or "mammal in need" include humans as well as non-human mammals, particularly domesticated animals including, without limitation, cats, dogs, and horses.

The term "therapeutically effective amount" is used to denote treatments at dosages effective to achieve the therapeutic result sought. Furthermore, one of skill will appreciate that the therapeutically effective amount of the compound of the invention may be lowered or increased by fine-tuning and/or by administering more than one compound of the invention, or by, administering a compound of the invention with another anti-asthmatic compound (e.g., corticosteroid). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect. Clinical changes relevant to assess the therapeutic effect of treatment according to the invention include reduction in the characteristic symptoms and signs of asthma and related pathologies (e.g., dyspnea, wheezing, cough, bronchial hypersensitivity airway remodeling) and improvement of pulmonary function tests. These are based upon patient's symptoms and physician's observations.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable, which is described as having values between 0 and 2, can be 0, 1 or 2 for variables which are inherently discrete, and can be 0.0, 0.1, 0.01, 0.001, or any other real value for variables which are inherently continuous.

For local administration by inhalation for example, contemplated therapeutically effective amounts are from about 0.1 μg/kg/day to about 1000 μg/kg/day when administered systemically (e.g., orally administered). In an embodiment of the invention, when systemically administer, therapeutically effective amounts are from about 0.5 μg/kg/day to about 200 μg/kg/day.

Dosage forms and frequency of administration of the same, will depend on conventional factors routinely considered by one of skill in the field to obtain therapeutically effective amounts as discussed above in a given mammal. Hence, a practitioner will consider the condition being treated, the particular compound of the invention being administered, route of administration, and other clinical factors such as age, weight and condition of the mammal as well as convenience and patient compliance.

It will be appreciated by those of skill in the art that the number of administrations of the compounds according to the invention will vary from patient to patient based on the particular medical status of that patient at any given time.

When applicable (such as for the treatment of asthma, for example) the compound according to this aspect of the invention, may be administered prior to, at the same time, or after the mammal has been exposed to an antigen. In addition, the timing of the administration of the compound of the invention with relation to the exposure to an antigen will vary from mammal to mammal depending on the particular situation. A skilled practitioner will optimize administration by careful monitoring the patient while altering the timing and/or the order of administration of the compound of the invention. Hence, it will be understood that the mammal need not suffer from a pulmonary inflammation to benefit from the invention. The compounds of the invention may be administered prophylactically to individuals predisposed to develop asthma and/or an asthma-related pathology. For example, an individual allergic to pollen may be administered a compound of the invention (e.g., by oral administration) on a daily basis and/or prior to going to a pollen-rich area (e.g., a garden). Likewise, an individual with only a family history of asthmatic attacks may be administered the compounds of the invention prophylactically—to prevent or inhibit possible onset of such an asthmatic attack.

Based on the above facts, the present invention also provides a method of treating acute and chronic inflammatory disorders of the airways of mammals—including asthma and asthma-related pathologies. This method comprises administering to a mammal in need of such treatment a therapeutically effective amount of a compound of formula (I)

The compounds according to the invention are optimally formulated in a pharmaceutically acceptable vehicle with any of the well-known pharmaceutically acceptable carriers, including diluents and excipients (see *Remington's Pharmaceutical Sciences*, 18$^{th}$ Ed., Gennaro, Mack Publishing Co., Easton, Pa. 1990 and *Remington: The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention, as well as any other pharmacologically active ingredient useful for the treatment of the particular pulmonary inflammation being treated. Such compounds may include without limitation, β-andrenoceptor antagonists: albuterol, metaproteranol, levalbuterol, pirbuterol, salmeterol, bitolterol; glucocorticoids: beclomethasone, triamcinolone, flunisolide, budesonide, fluticasone; leukotriene-receptor antagonists and leukotriene-synthesis inhibitors: zafirlukast, montelukast, zileutin; other anti-asthmatics: cromolyn, nedocromil, theophylline; anti-cholinergic agents: ipatropium, oxitropium, tiotropium; $H_1$ receptor antagonist anti-histamines: diphenydramine, pyrilamine, promethazine, loratidine, chlorocyclizine, chlorophemiramine, fexofenadine and adrenocorticosteroids.

The compositions of the invention can be administered by standard routes (e.g. oral, inhalation, rectal, nasal, topical, including buccal and sublingual, or parenteral, including subcutaneous, intramuscular, intravenous, intradermal, transdermal, and intratracheal). In addition, polymers may be added according to standard methodologies in the art for sustained release of a given compound.

Formulations suitable for administration by inhalation include formulations that can be dispensed by inhalation devices known to those in the art. Such formulations may include carriers such as powder and aerosols. The present invention encompasses liquid and powdered compositions suitable for nebulization and intrabronchial use, or aerosol compositions administered via an aerosol unit dispensing metered doses ("MDI"). Particularly preferred devices contemplated are described in U.S. Pat. No.: 5,447,150.

The active ingredient may be formulated in an aqueous pharmaceutically acceptable inhalant vehicle, such as, for example, isotonic saline or bacterostatic water and other types of vehicles that are well known in the art. The solutions are administered by means of a pump or squeeze-actuated nebulized spray dispenser, or by any other conventional means for causing or enabling the requisite dosage amount of the liquid composition to be inhaled into the patient's lungs.

Powder compositions containing the anti-inflammatory compounds of the present invention include, by way of illustration, pharmaceutically acceptable powdered preparations of the active ingredient thoroughly intermixed with lactose or other inert powders acceptable for intrabronchial administration. The powder compositions can be administered via a dispenser, including, but not limited to, an aerosol dispenser or encased in a breakable capsule, which may be inserted by the patient into a device that punctures the capsule and blows the powder out in a steady stream.

Aerosol formulations for use in the subject method typically include propellants, surfactants, and co-solvents and may be filled into conventional aerosol containers that are closed by a suitable metering valve.

For oral administration, the anti-inflammatory compositions of the invention may be presented as discrete units such as capsules, caplets, gelcaps, cachets, pills, or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc. Alternately, administration of a composition of all of the aspects of the present invention may be effected by liquid solutions, suspensions or elixirs, powders, lozenges, micronized particles and osmotic delivery systems.

Formulations of compositions of the present invention suitable for nasal administration, wherein the carrier is a solid, include a coarse powder having a particle size, for example, in the range of 20 to 500 microns which is administered in the manner in which snuff is administered, i.e. by rapid inhalation through the nasal passage from a container of the powder held close up to the nose. Suitable formulations, wherein the carrier is a liquid, for administration, for example via a nasal spray, aerosol, or as nasal drops, include aqueous or oily solutions of the compound of the invention. Semi-liquid formulations, such as a nasal gel, are also suitable.

Formulations of compositions suitable for parenteral administration include aqueous and non-aqueous sterile injection solutions which may contain antioxidants, stabilizer, buffers, bacteriostats and solutes which render the formulation isotonic with the blood of the intended recipient; and aqueous and non-aqueous sterile suspensions which may include suspending agents and thickening agents.

The process for the synthesis of compounds of the general formula (IA), (IB) and (IC), which are stereochemically defined representatives of compounds of the general formula (I) of the present invention, is illustrated by the following examples.

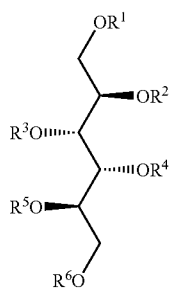
(IA)

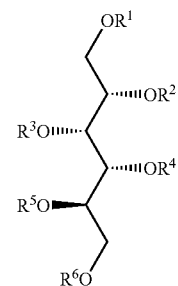
(IB)

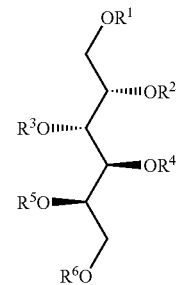
(IC)

Compounds of formula VIII, IX, XIV, XVIII, XIX, XX, XXI, XXIV, XXIX, XXXIII, XXXVII, XLIII, XLV, XLVII, IL, LIII, LVII and LXI used as starting compounds in the examples, are concrete, stereochemically defined, isomerically pure representatives of formula (II). Chemical structures thereof are demonstrated below:

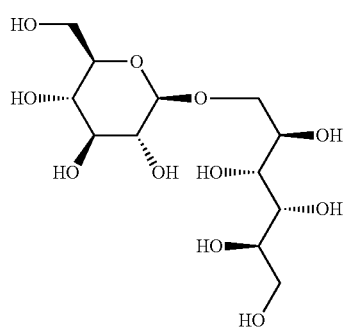
(VIII)

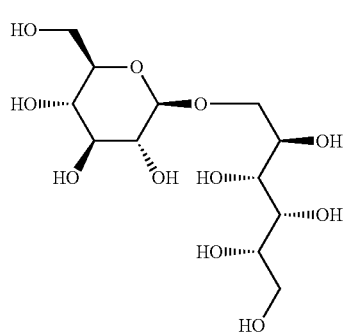 = 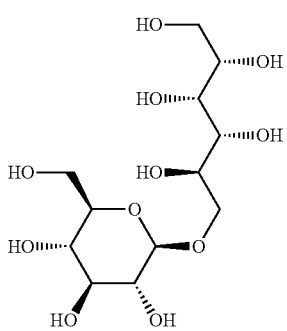
(IX)

-continued
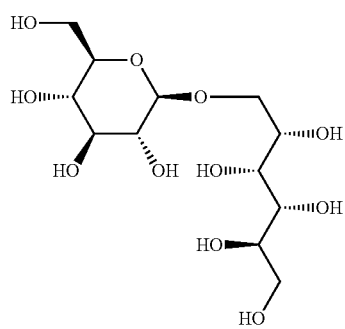
(XIV)
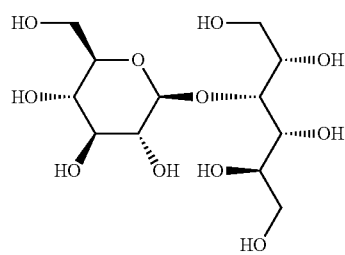
(XVIII)
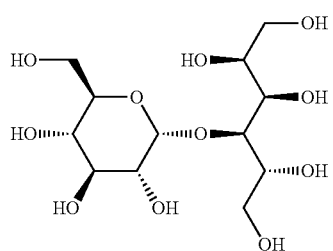
(XIX)
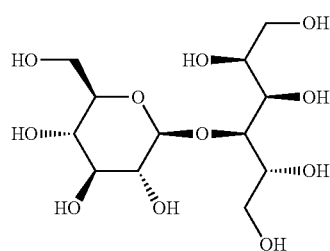
(XX)
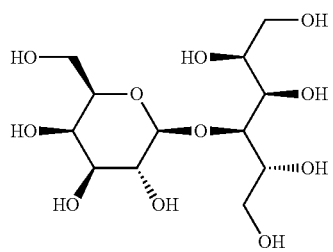
(XXI)
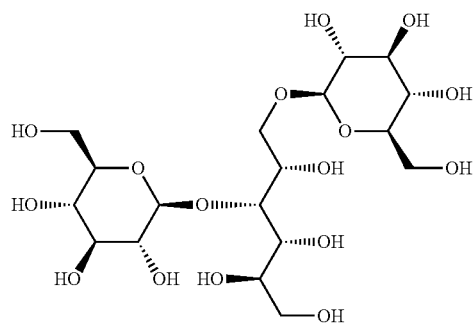
(XXIV)
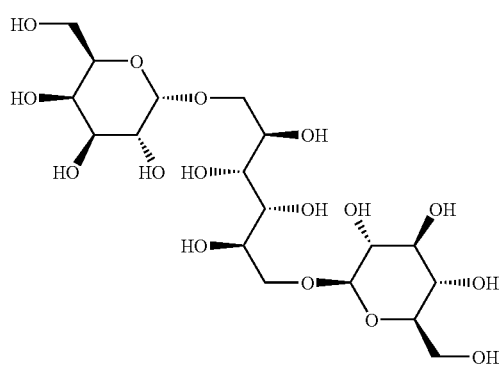
(XXIX)
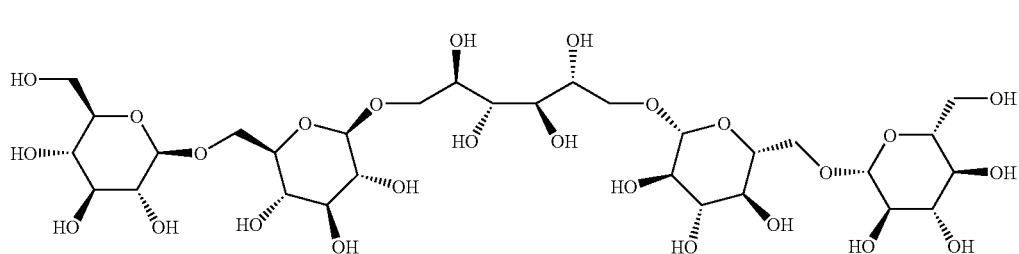
(XXXIII)

(XXXVII)
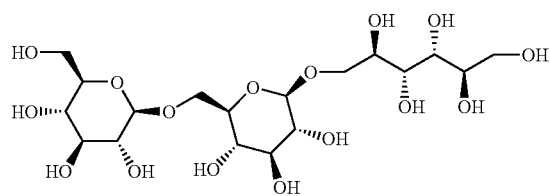
(XLIII)
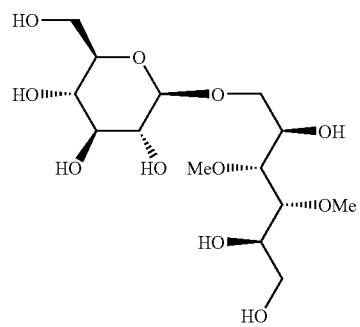
(XLV)
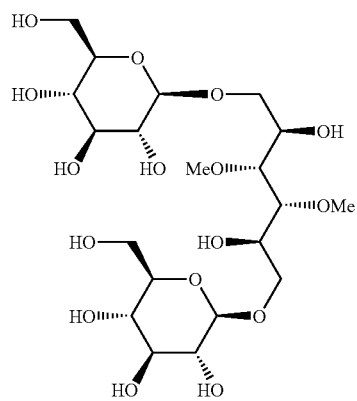
(XLVII)
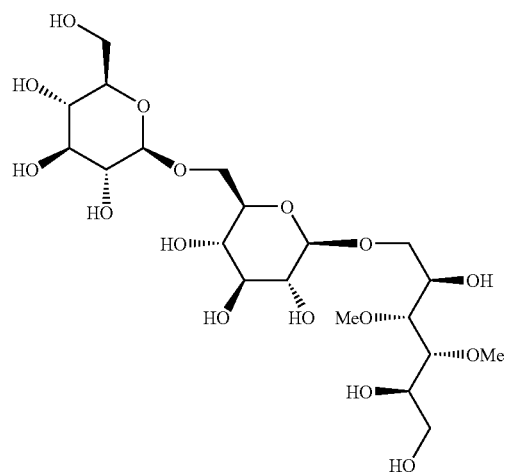
(IL)
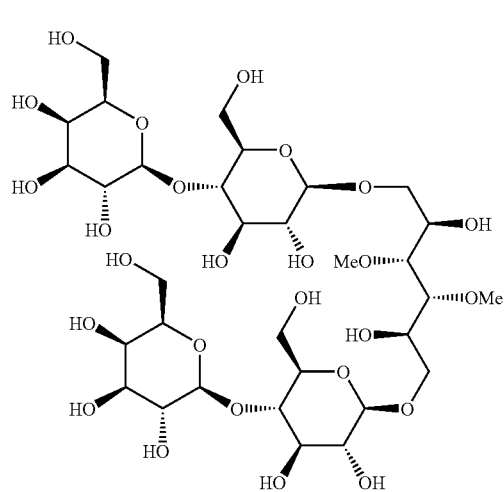
(LIII)
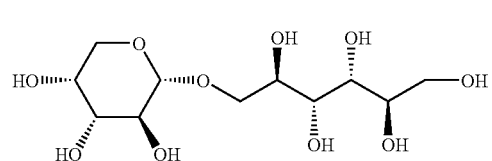

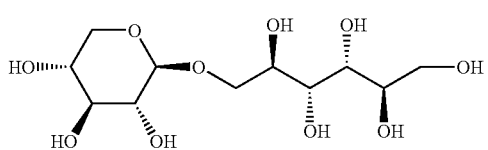
(LVII)

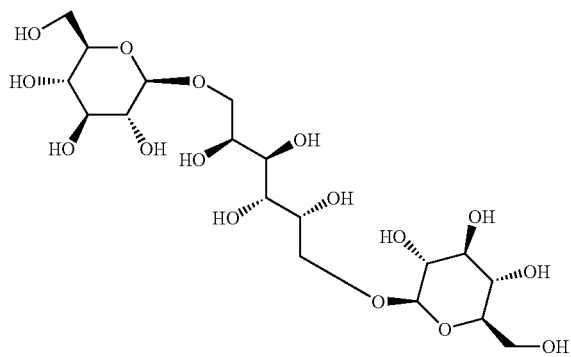
(LXI)

Compounds of formula XI, XII, XIII, XV, XVI, XVII, XXII, XXIII, XXV, XXVI, XXVII, XXVIII, XXXI, XXXII, XXXIX, XXXV, XXXVI, XXXVIII, XKI, XLII, XLIV, XLVI, XLVIII, LI, LII, LV, LVI, LVIII, LIX and LX, which are used in the synthesis of the new starting materials of formula (U), are concrete, stereochemically defined, isomerically pure representatives of formula (V). Chemical structures-thereof are demonstrated below:

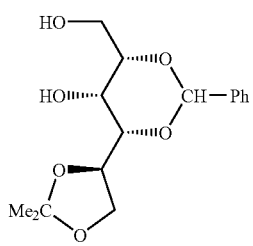
(XI)

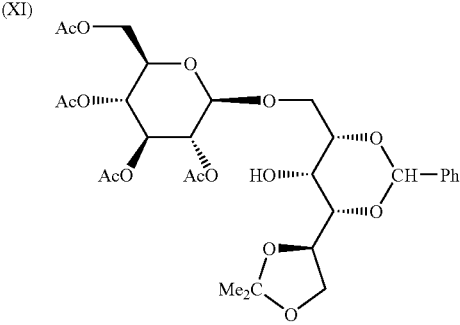
(XII)

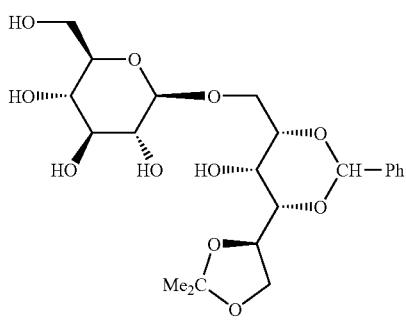
(XIII)

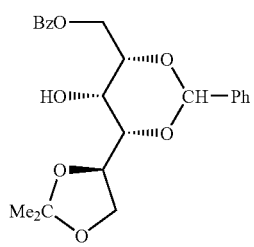
(XV)

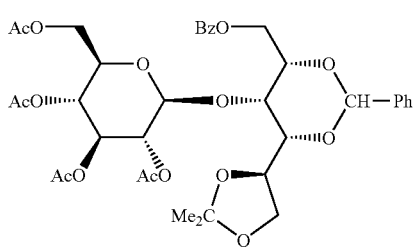
(XVI)

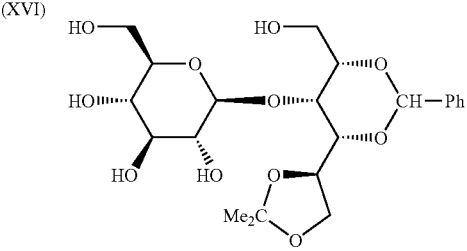
(XVII)

-continued
(XXII)
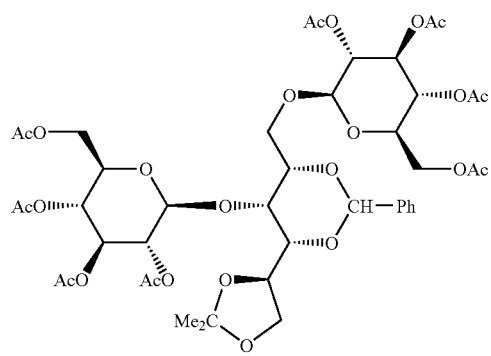
(XXIII)
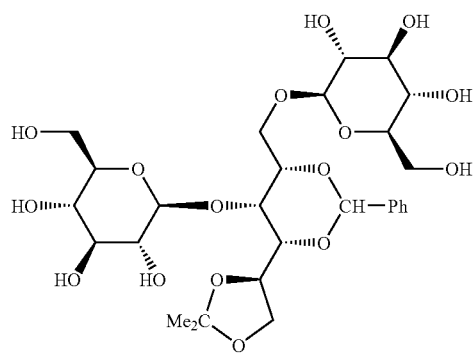
(XXVI)
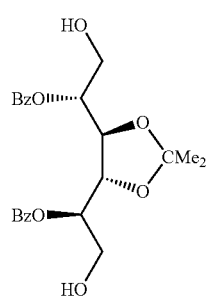
(XXVII)
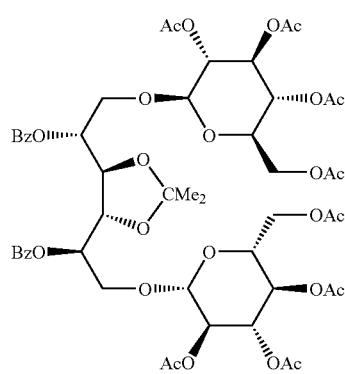
(XXVIII)
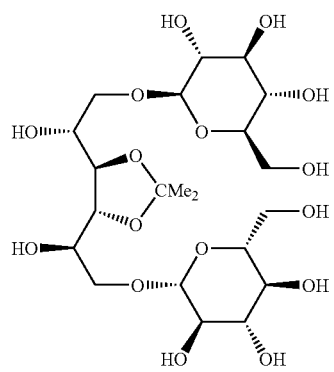
(XXXI)
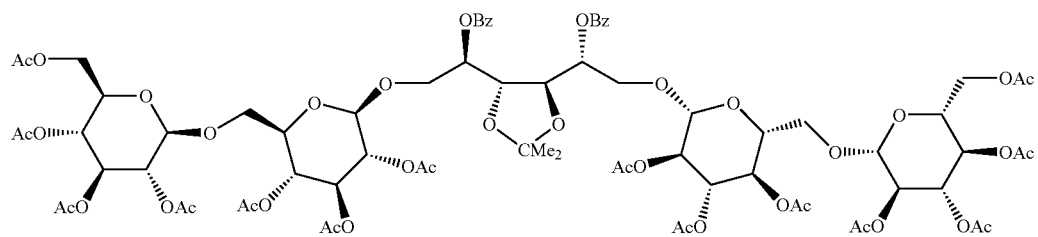
(XXXII)
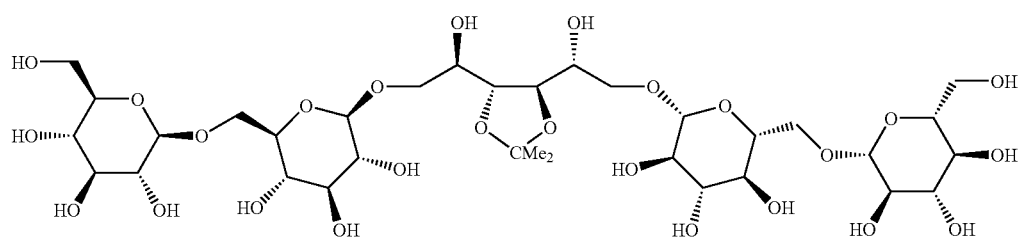

-continued
(XXXIV)
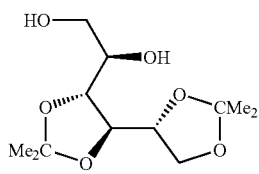
(XXXV)
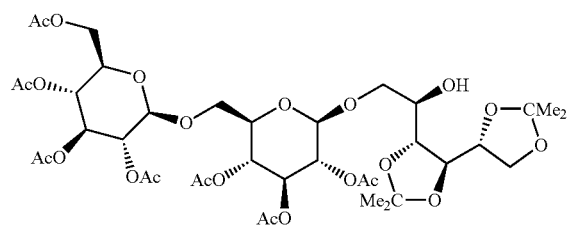
(XXXVI)
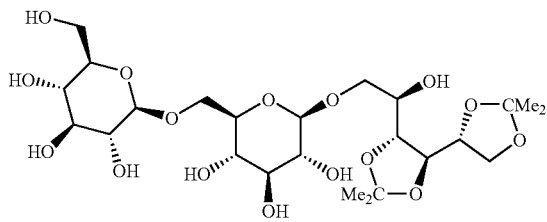
(XLI)
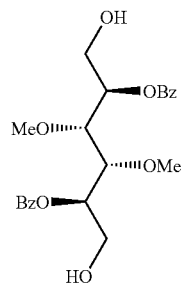
(XLII)
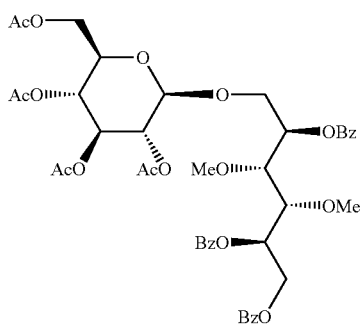
(XLIV)
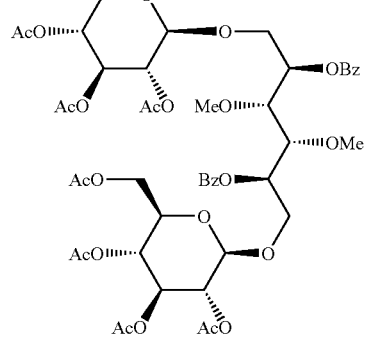
(XLVI)
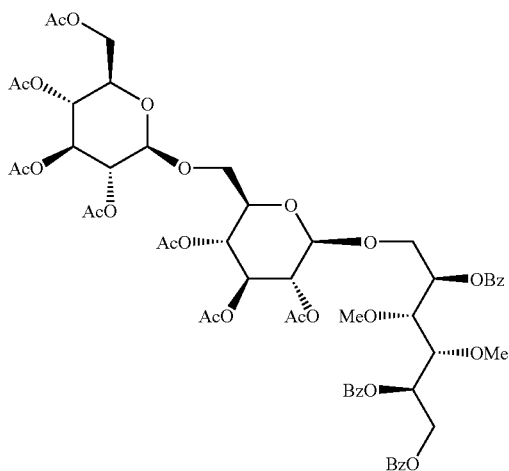
(XLVIII)
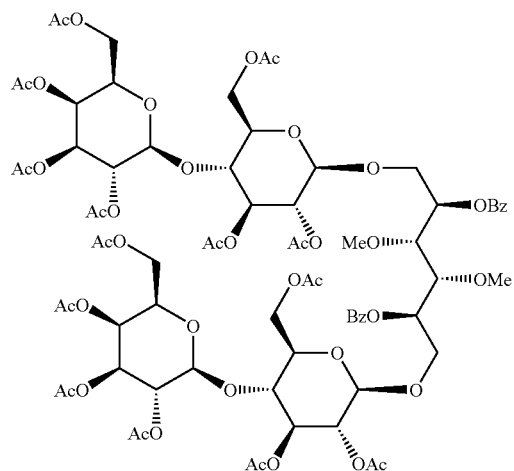
(LI)
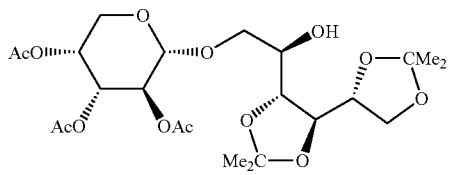
(LII)
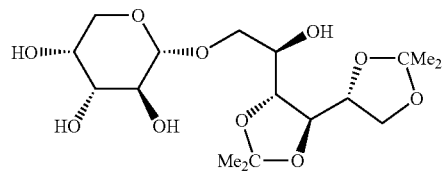

-continued
(LV)
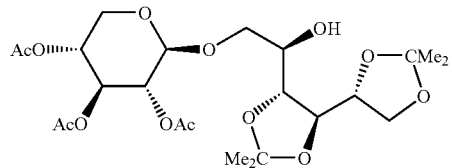
(LVI)
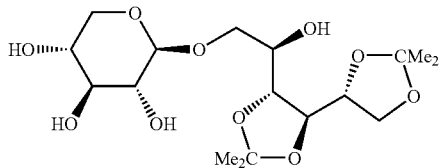
(LVIII)
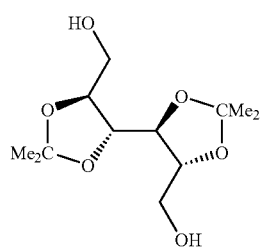
(LIX)
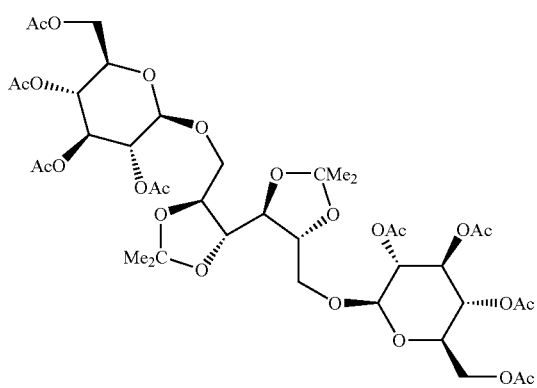
(LX)
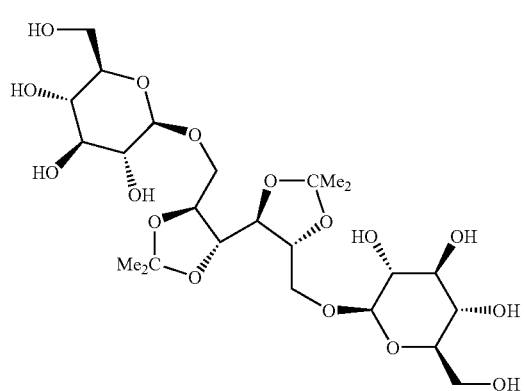

The donor molecules used in the glycosylation reactions are either commercially available, for example the compound of formula (X)

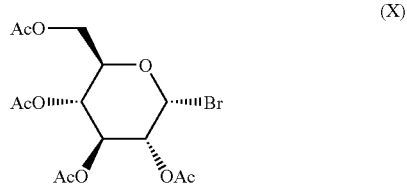

or can be synthesized by known methods (see experimental part), for example compounds of formula (XXX), (L) and (LIV).

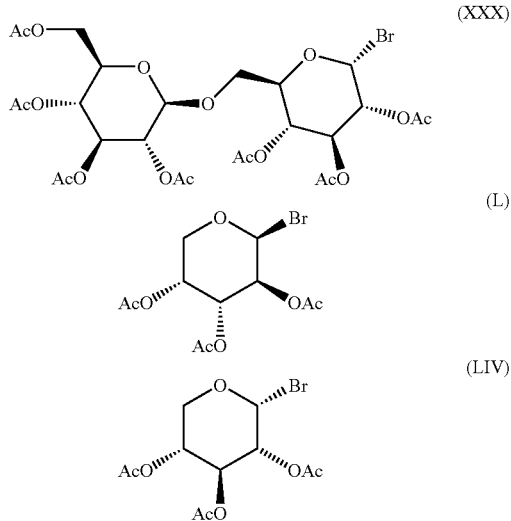

The $R^f$ values given in the examples were determined by thin layer chromatography using silica gel (DC-Alufolien Kieselgel 60 $F_{254}$, Merck, Darmstadt) and the following mixtures of solvents:
(A) Ethyl acetate-hexane 1:1
(B) Ethyl acetate-hexane 1:2
(C) Ethyl acetate-hexane 2:1
(D) Ethyl acetate-hexane 3:1
(E) Ethyl acetate-methanol 1:1
(F) Ethyl acetate-methanol 3:1
(G) Ethyl acetate-methanol 5:1

The spots were detected either in UV light or by spraying the plates with a 1:1 mixture of 0.1 M $KMnO_4$-1 M $H_2SO_4$ followed by heating to 200° C. Column chromatography was performed on Kieselgel 60. Optical rotations were measured at 20° C. NMR spectra were recorded with Bruker Avance 500 MHz spectrometer using $Me_4Si$ as the internal standard. The assignments of the protons were based on COSY, 2D and selective 1D TOCSY as well as selective 1D NOESY experiments. Multiplicities of the $^{13}C$ spectra were obtained from DEPT experiments. Connectivities between identified protons and protonated carbons were observed by means of HMQC and HMBC experiments.

In the case of acylation reactions carried out in the presence of pyridine the "usual work-up" means that if the product is not crystalline after pouring the reaction mixture into ice-water, it is extracted with an organic solvent, the organic layer is washed with water, 1 M ice-cold aqueous sulfuric acid solution until permanent acidity, water, 5% aqueous sodium bicarbonate solution and water, dried, filtered and the solvent is evaporated in vacuum.

Starting material for a compound of formula (XIV) is synthesized for example by the following method:
Step a)

2,4-O-benzylidene-5,6-O-isopropylidene-D-glucitol
(XI)

To a stirred suspension of 27 g (0.1 mol) of 2,4-O-benzylidene-D-glucitol (L. Vargha, Ber. 68 (1935) 18-24) in 150 ml of dimethylformamide 20 ml (0.26 mol) of 2,2-dimethoxypropane and 100 mg of p-toluenesulfonic acid were added at room temperature. After stirring for 10 min a clear solution was obtained and 1 ml of triethylamine was added after 1 h. The reaction mixture was concentrated, the residue was dissolved in chloroform, the insoluble starting material was filtered off, the filtrate was concentrated and residue was recrystallized from 200 ml of benzene to yield 14 g (45%) of the title compound. Mp.: 178° C., $R_f$ 0.4 (solvent C).
Step b)

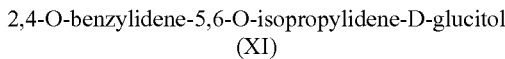

To a solution of 3.1 g (10 mmol) of the product of formula (XI) obtained in the previous step in 50 ml of acetonitrile 7 g of molecular sieves (4 Å) was added and the mixture was stirred at room temperature for 30 min. Then 4.5 g (11 mmol) of acetobromo-D-glucose (X) and 3 g (12 mmol) of $Hg(CN)_2$ were added and the mixture was stirred at room temperature for 20 h. Then the reaction mixture was filtered and the filtrate was diluted with 100 ml of chloroform, washed with 5% aqueous sodium bicarbonate solution, 10% aqueous potassium bromide solution and water, dried and concentrated. The residue is purified by column chromatography (solvent C) to yield 2.7 g (42%) of the title compound, $R_f$ 0.7, $[\alpha]_D$ +5° (c 1, chloroform).
Step c)

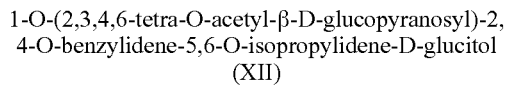

To a solution of 4.1 g of the product of formula (XII) obtained in the previous step in 40 ml of methanol 0.5 ml of 2 M sodium methoxide solution in methanol was added at room temperature. After 2 h sodium ions were removed by addition of cation exchange resin, the mixture was filtered and the filtrate was concentrated. The residue was purified by column chromatography (solvent G) to yield 2.2 g (73%) of the title compound, $R_f$ 0.6, $[\alpha]_D$ –8° (c 1, chloroform).
Step d)

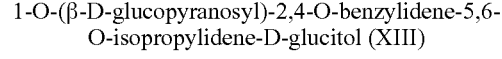

To a stirred solution of 3 g of the product of formula (XIII) obtained in the previous step in 80 ml of methanol, 3 ml of water, 1 ml of acetic acid and 2 g of 10% Pd/C catalyst was added and the mixture was hydrogenated at atmospheric pressure. When according to TLC the reaction was complete (~4 h), the catalyst was filtered off, the filtrate was concentrated, the residue was dissolved in 20 ml of 0.05 M sulfuric acid and stirred at 60° C. for 90 min. The cooled solution was neutralized by addition of ion-exchange resin, filtered, concentrated to a volume of 15 ml and freeze-dried to yield 1.9 g (86%) of the title compound, $R_f$ 0.1 (solvent E), $[\alpha]_D$ −105° (c 1, water).

The starting material of formula (XVM) can be synthesized for example by the following method:

Step a)

2,4-O-benzylidene-1-O-benzoyl-5,6-O-isopropylidene-D-glucitol (XV)

To a stirred solution of 3.1 g (10 mmol) of 2,4-O-benzylidene-5,6-O-isopropylidene-D-glucitol (L. Vargha, Ber. 68 (1935) 18-24 and 1377-1384) in 10 ml of pyridine 1.3 ml (11 mmol) of benzoylchloride was added dropwise at −20° C. The reaction mixture was stirred at this temperature for 15 min and at room temperature for 30 min, then worked up the usual way. The residue obtained after concentration of organic phase was purified by column chromatography (solvent B) to yield 2.5 g (60%) of the title compound as colourless syrup, $R_f$ 0.6, $[\alpha]_D$ −24° (c 1, chloroform).

Step b)

3-O-(2,3,4,6-tetra-O-acetyl-β-D-glucopyranosyl)-2,4-O-benzylidene-1-O-benzoyl-5,6-O-isopropylide-D-glucitol (XVI)

To a stirred solution of 2.5 g (6 mmol) of the product of formula (XV) obtained in the previous step in 20 ml of acetonitrile 5 g of molecular sieves (4 Å) was added and the mixture was stirred at room temperature for 30 min. Then 2.5 g (6 mmol) of acetobromo-D-glucose (X) and 1.6 g (6.5 mmol) of Hg(CN)$_2$ were added and the mixture was stirred at room temperature fbr 20 h. Then the reaction mixture was filed and the filtrate was diluted with 40 ml of chloroform, washed with 5% aqueous sodium bicarbonate solution, 10% aqueous potassium bromide solution and water, dried and concentrated. The residue is purified by column chromatography (solvent A) to yield 2.45 g (55%) of the title compound, $R_f$ 0.5, $[\alpha]_D$ −4° (c 1, chloroform).

Step c)

3-O-(β-D-glucopyranosyl)-D-glucitol (XVIII)

To a solution of 4.46 g (6 mmol) of the product of formula (XVI) obtained in the previous step in 20 ml of methanol 0.2 ml of 2-M sodium methoxide solution in methanol was added at room temperature. After 1 h, when according to TLC the deacylation was complete, sodium ions were removed by addition of cation exchange resin, the mixture was filtered and the filtrate was concentrated. The residue, which contained the deacylated product (XVII) and methyl benzoate, was dissolved in 50 ml of methanol, 3 ml of water, 1 ml of acetic acid and 2 g of 10% Pd/C catalyst were added and the mixture was hydrogenated at atmospheric pressure. When according to TLC the reaction was complete (~15 h), the catalyst was filtered off, the filtrate was concentrated, the residue was dissolved in a mixture of chloroform and water and separated. 1.5 ml of sulfuric acid was added to the aqueous phase and stirred at 60° C. for 1 h. The cooled solution was neutralized by addition of ion-exchange resin, filtered, concentrated to a volume of 15 ml and freeze-dried to yield 2 g (97%) of the title compound as hygroscopic powder, which was used in the next step without further purification. $[\alpha]_D$ −14° (c 1, water).

The starting material of formula (XXIV) can be synthesized for example by the following method:

Step a)

1,3-bis-O-(2,3,4,6-tetra-O-acetyl-β-D-glucopyranosyl)-2,4-O-benzylidene-5,6-O-isopropylidene-D-glucitol (XXII)

To a solution of 6.2 g (20 mmol) of 2,4-O-benzylidene-5,6-O-isopropylidene-D-glucitol (XI) in 200 ml of acetonitrile 24 g of molecular sieves (4 Å) was added and the mixture was stirred at room temperature for 30 min. Then 18 g (44 mmol) of acetobromo-D-glucose (X) and 12 g (48 mmol) of Hg(CN)$_2$ were added and the mixture was stirred at room temperature for 20 h. Then the reaction mixture was filtered and the filtrate was diluted with 400 ml of chloroform, washed with 5% aqueous sodium bicarbonate solution, 10% aqueous potassium bromide solution and water, dried and concentrated. The residue is recrystallized from 150 ml of methanol to yield 1.8 g (9.3%) of the title compound. Mp.: 168-170° C., $R_f$ 0.7 (solvent C), $[\alpha]_D$ −5° (c 1, chloroform).

Step b)

1,3-bis-O-(β-D-glucopyranosyl)-2,4-O-benzylidene-5,6-O-isopropylidene-D-glucitol (XXXIII)

To a solution of 2.65 g of the product of formula (XXII) obtained in the previous step in 30 ml of methanol 0.5 ml of 2 M sodium methoxide solution in methanol was added at room temperature. After 2 h sodium ions were removed by addition of cation exchange resin, the mixture was filtered and the filtrate was concentrated to yield 1.7 g (97%) of the title compound, $R_f$ 0.3 (solvent F), $[\alpha]_D$ −8° (c 1, chloroform).

Step c)

1,3-bis-O-(β-D-glucopyranosyl)-D-glucitol (XXIV)

To a stirred solution of 1.7 g of the product of formula (XXIII) obtained in the previous step in 50 ml of methanol 3 ml of water, 1 ml of acetic acid and 1 g of 10% Pd/C catalyst were added and the mixture was hydrogenated at atmospheric pressure. When according to TLC the reaction was complete (~4 h), the catalyst was filtered off, the filtrate was concentrated, the residue was dissolved in 20 ml of 0.05 M sulfuric acid and stirred at 60° C. for 90 min. The cooled solution was neutralized by addition of ion-exchange resin, filtered, concentrated to a volume of 15 ml and freeze-dried to yield 1.25 g (92%) of the title compound. $R_f$ 0.1 (solvent E), $[\alpha]_D$ −20° (c 1, water).

The starting material of formula (XXIX) can be synthesized for example by the following method:

Step a)

2,5-di-O-benzoyl-3,4-O-isopropylidene-1,6-di-O-trityl-D-mannitol (XXV)

To a stirred solution of 11.1 g (50 mmol) of 3,4-O-isopropylidene-D-mannitol (T. Horváth and L. Vargha, Carbohydr. Res., 16 (1971) 253-259) in 50 ml of pyridine 33.4 g (120 mmol) of trityl chloride was added at room temperature. After 2 days 14 ml of benzoyl chloride was added dropwise to the reaction mixture below 20° C. After 2 h the reaction mixture was poured into ice-water, the water was decanted from the precipitated syrupy material and the residue was crystallized with 400 ml of ethanol. The crystalline material was filtered off, washed with ethanol and dried. The so obtained product was recrystallized from 2.5-fold ethyl acetate to yield 36.1 g (79%) of the title compound. Mp.: 165-167° C., $[\alpha]_D$ +7° (c 1, chloroform).

Step b)

2,5-di-O-benzoyl-3,4-O-isopropylidene-D-mannitol (XXVI)

To a solution of 30 g (33 mmol) of the product of formula (XXV) obtained in the previous step in 300 ml of dioxane 50 ml of 0.1 M sulfuric acid was added and the solution was stirred at 90° C. for 6 h. The cooled solution, was neutralized by addition of ion-exchange resin, filtered and concentrated. The residue was purified by column chromatography (solvent A) and the obtained crude product was recrystallized from ether-hexane to yield 3.3 g (23.6%) of the title compound. Mp.: 97-99° C., $R_f$ 0.45, $[\alpha]_D$ −20° (c 1, chloroform).

Step c)

1,6-bis-O-(2,3,4,6-tetra-O-acetyl-β-D-glucopyranosyl)-2,5-di-O-benzoyl-3,4-O-isopropylidene-D-mannitol (XXVII)

To a solution of 3 g (7 mmol) of the product of formula (XXVI) obtained in the previous step in, 65 ml of acetonitrile 7 g of molecular sieves (4 Å) was added and the mixture was stirred at room temperature for 30 min. Then 6.5 g (16 mmol) of acetobromo-D-glucose (X) and 4.4 g (18 mmol) of Hg(CN)$_2$ were added and the mixture was stirred at room temperature for 20 h. Then the reaction mixture was filtered and the filtrate was diluted with 130 ml of chloroform, washed with 5% aqueous sodium bicarbonate solution, 10% aqueous potassium bromide solution and water, dried and concentrated. The residue was purified by column chromatography (solvent C) and the obtained crude product was recrystallized from ethanol to yield 2.75 g (36%) of the title compound. Mp.: 193-195° C., $R_f$ 0.4, $[\alpha]_D$ −28° (c 1, chloroform).

Step d)

1,6-bis-O-(β-D-glucopyranosyl)-D-mannitol (XXIX)

To a stirred solution of 2.6 g (2.4 mmol) of the product of formula (XXVII) obtained in the previous step in 40 ml of methanol 0.5 ml of 2 M sodium methoxide solution in methanol was added at room temperature. After 1 h sodium ions were removed by addition of cation exchange resin, the mixture was filtered and the filtrate was concentrated. The residue was dissolved in water and extracted with chloroform in order to remove methyl benzoate. The aqueous solution containing the compound of formula (XXVII) was concentrated to a volume of 15 ml and 1.5 ml of 1 M sulfuric acid was added. The solution was stirred at 60° C. for 90 min, then cooled and neutralized by addition of ion-exchange resin. The filtered solution was freeze-dried to yield 1.15 g (95%) of the title compound as amorphous powder. $[\alpha]_D$ −23.4° (c 1, water).

The starting material of formula (XXXIII) can be synthesized for example by the following method:

Step a)

1,6-bis-O-(2,3,4,2',3',4',6'-hepta-O-acetyl-β-gentiobiopyranosyl)-2,5-di-O-benzoyl-4,5-O-isopropylidene-D-mannitol (XXXI)

To a stirred solution of 1.72 g (4 mmol) of 2,5-dibenzoyl-3,4-O-isopropylidene-D-mannitol (XXVI, described above) in 60 ml of acetonitrile 7 g of molecular sieves (4 Å) was added and the mixture was stirred at room temperature for 30 min. Then 6 g (8.6 mmol) of acetobromo gentiobiose (XXX) (K. Takiura, S. Honda. T. Endo, K. Kakehi. Chem. Pharm. Bull. 20 s 1972) 438-442) and 4.4 g (18 mmol) of Hg(CN)$_2$ were added and the mixture was stirred at room temperature for 20 h. Then the reaction mixture was filtered and the filtrate was diluted with 120 ml of chloroform, washed with 5% aqueous sodium bicarbonate solution, 10% aqueous potassium bromide solution and water, dried and concentrated. The residue was purified by column chromatography (solvent D) and the obtained crude product was recrystallized from ethanol to yield 1.3 g (22%) of the title compound. Mp.: >220° C., $R_f$ 0.5, $[\alpha]_D$ −16° (c 1, chloroform).

Step b)

1,6-bis-O-(β-D-gentiobiopyranosyl)-D-mannitol (XXXIII)

To a solution of 1.3 g (0.78 mmol) of the product of formula (XXXI) obtained in the previous step in 25 ml of methanol 025 ml of 2 M sodium methoxide solution in methanol was added and the reaction mixture was stirred at 45° C. for 2 h. After cooling sodium ions were removed by addition of cation exchange resin, the mixture was filtered and the filtrate was concentrated. The residue was dissolved in water and extracted with chloroform in order to remove methyl benzoate. The aqueous solution containing the compound of formula (XXXII) was concentrated to a volume of 15 ml and 1.5 ml of M sulfuric acid was added. The solution was stirred at 60° C. for 90 min, then cooled and neutralized by addition of ion-exchange resin. The filtered solution was freeze-dried to yield 0.65 g (~100%) of the title compound as amorphous powder. $[\alpha]_D$ 3.5° (c 1, water).

The starting material of formula (XXXVII) can be synthesized for example by the following method:

Step a)

1-O-(2,3,4,2',3,4,6'-hepta-O-acetyl-β-gentiobiopyranosyl)-3,4:5,6-O-isopropylidene-D-mannitol (XXXV)

To a solution of 2.4 g (9.2 mmol) of 1,2:3,4-di-O-isopropylidene-D-mannitol (XXXIV) (L. F. Wiggins, J. Chem. Soc (1946) 13-14) in 60 ml of acetonitrile 7 g of molecular sieves (4 Å) was added and the mixture was stirred at room temperature for 30 min. Then 6.3 g (9 mmol) of acetobromo gentiobiose (XXX) (K. Takiura, S. Honda, T. Endo, K. Kakehi. Chem. Pharm. Bull. 20 (1972) 438-442) and 2.5 g (10 mmol) of Hg(CN)$_2$ were added and the mixture was stirred at room temperature for 20 h. Then the reaction mixture was filtered and the filtrate was diluted with 120 ml of chloroform, washed with 5% aqueous sodium bicarbonate solution, 10% aqueous potassium bromide solution and water, dried and concentrated. The residue was purified by column chromatography (solvent C) to yield 4.1 g (52%) of the title compound. $R_f$ 0.4, $[\alpha]_D$ +2° (c 1, chloroform).

Step b)

1-O-β-gentiobiopyranosyl-3,4:5,6-di-O-isopropylidene-D-mannitol (XXXVI)

To a stirred solution of 3.9 g (4.4 mmol) of the product of formula (XXXV) obtained in the previous step in 50 ml of methanol 0.5 ml of 2 M sodium methoxide solution in methanol was added at room temperature. After 2 h sodium ions were removed by addition of cation exchange resin, the mixture was filtered and the filtrate was concentrated. The residue was purified by column chromatography (solvent F) to yield 1.6 g (62%) of the title compound. $R_f$ 0.4, $[\alpha]_D$ −5.5° (c 1, water).

Step c)

1-O-β-gentiobiopyranosyl-D-mannitol (XXXVII)

A solution of 1.4 g (2.4 mmol) of the product of formula (XXXVI) obtained in the previous step in 20 ml of 0.01 M sulfuric acid was stirred at 60° C. for 1.5 h. The cooled solution was neutralized by addition of ion-exchange resin, filtered and freeze-dried to yield 1.15 g (95%) of the title compound. $[\alpha]_D$ −17° (c 1, water).

The starting material of formula (XLIII) can be synthesized for example by the following method:
Step a)

2,5-di-O-benzoyl-3,4-di-methyl-1,6-di-O-trityl-D-mannitol (XL)

To stirred solution of 6.3 g (20 mmol) of 3,4-di-O-methyl-D-mannitol (XLI) (J. Kuszmann, Carbohydr. Res., 71 (1979) 123-134) in 60 ml of pyridine 20.1 g 72 mmol) of trityl chloride was added. The reaction mixture was kept at room temperature for 2 days, then 8.4 ml of benzoyl chloride was added dropwise to the stirred and cooled solution. The reaction mixture was stirred at room temperature for 2 h, then poured into ice-water, extracted with dichloromethane and the organic layer was processed the usual way. The residue obtained after concentration was dissolved in 150 ml of hot ethanol, cooled, the precipitated product was filtered and washed with ethanol. The so obtained crude product was dissolved in 40 ml of ethyl acetate and 120 ml of ethanol was added. The precipitated product was filtered off and washed with ethanol to yield 20.25 g (75%) of the title compound. Mp.: 128-130° C., $[\alpha]_D$ +45° (c 1, chloroform).
Step b)

2,5-di-O-benzoyl-3,4-di-O-methyl-D-mannitol (XLI)

To a stirred solution of 20 g of the product of formula (XL) obtained in the previous step in 300 ml of hot acetic acid 100 ml of water was added in small portions and the mixture was stirred at 80-90° C. for 30 min. After cooling the precipitated trityl alcohol was filtered off and filtrate was extracted with chloroform. The organic layer was washed with water, 5% aqueous sodium bicarbonate solution, water, dried and concentrated. The residue was purified by column chromatography (solvent E) to yield 7.0 g (75.5%) of the title compound as syrup. $R_f$ 0.2, $[\alpha]_D$ +33° (c 1, chloroform)
Step c)

1-O-(2,3,4,6-tetra-O-acetyl-β-D-glucopyranosyl)-2,5,6-tri-O-benzoyl-3,4-di-O-methyl-D-mannitol (XLII)

To a stirred solution of 6.3 g (15 mmol) of 2,5-O-benzoyl-3,4-di)-O-methyl-D-mannitol (XLI) obtained in the previous step in 65 ml of acetonitrile 7 g of molecular sieves (4 Å) was added and the mixture was stirred at room temperature for 30 min. Then 6.2 g (15 mmol) of acetobromo-D-glucose (X) and 4.2 g (16 mmol) of Hg(CN)₂ were added and the mixture was starred at room temperature for 20 h. Then the reaction mixture was filtered and the filtrate was diluted with 130 ml of chloroform, washed with 5% aqueous sodium bicarbonate solution, 10% aqueous potassium bromide solution and water, dried and concentrated. The residue was dissolved in 50 ml of pyridine and 4 ml of benzoyl chloride was added dropwise to the stirred solution at room temperature. After 2 h the reaction mixture was poured into ice-water, extracted with dichloromethane and processed the usual way. The residue obtained on concentration was purified by column chromatography (solvent A) to yield 3.5 g (27%) of the title compound as syrup. $R_f$ 0.6, $[\alpha]_D$ 0° (C₁, chloroform).
Step d)

1-O-(β-D-glucopyranosyl)-3,4-di-O-methyl-D-mannitol (XLIII)

To a stirred solution of 3.3 g (2.87 mmol) of the product of formula (XLII) obtained in the previous step in 40 ml of methanol 0.5 ml of 2 M sodium methoxide solution in methanol was added and the reaction mixture was refluxed for 2 h. After cooling sodium ions were removed by addition of cation exchange resin, the mixture was filtered and the filtrate was concentrated. The residue was dissolved in water and extracted with chloroform in order to remove methyl benzoate. The aqueous solution was concentrated to a volume of 20 ml and freeze-dried to yield 1.4 g (97%) of the title compound as amorphous powder. $[\alpha]_D$+10° (C₁, water).

The starting material of formula (XLV) can be synthesized for example by the following method:
Step a)

1,6-bis-O-β-(2,3,4,6-tetra-O-acetyl-β-D-glucopyranosyl)-2,5-di-O-benzyl-3,4-di-O-methyl-D-mannitol (XLIV)

To a stirred solution of 3.34 g (8 mmol) of 2,5-di-O-benzoyl-3,4-di-O-methyl-D-mannitol (XLI, described above) in 65 ml of acetonitrile 7 g of molecular sieves (4 Å) was added and the mixture was stirred at room temperature for 30 min. Then 8.2 g (20 mmol) of acetobromo-D-glucose (X) and 5.5 g (22 mmol) of Hg(CN)₂ were added and the mixture was stirred at room temperature for 20 h. Then the reaction mixture was filtered and the filtrate was diluted with 130 ml of chloroform, washed with 5% aqueous sodium bicarbonate solution, 10% aqueous potassium bromide solution and water, dried and concentrated. The residue was purified by column chromatography (solvent C) and the obtained crude product was recrystallized from ethanol to yield 3.4 g (39%) of the title compound. Mp.: 138-140° C., $R_f$ 0.35, $[\alpha]_D$ +38° (c 1, chloroform).
Step b)

1,6 bis-O-β-D-glucopyranosyl-3,4-di-O-methyl-D-mannitol (XLV)

To a stirred solution of 3.1 g (2.87 mmol) of the product of formula (XLIV) obtained in the previous step in 40 ml of methanol 0.5 ml of 2 M sodium methoxide solution in methanol was added at room temperature. After 2 h sodium ions were removed by addition of cation exchange resin, the mixture was filtered and the filtrate was concentrated. The residue was dissolved in water and extracted with chloroform in order to remove methyl benzoate. The aqueous solution was concerted to a volume of 15 ml and freeze-dried to yield 1.56 g (~100%) of the title compound as amorphous powder. $[\alpha]_D$ −4° (c 1, water).

The starting material of formula (XLVII) can be synthesized for example by the following method:
Step a)

1-O-(2,3,4,2',3',4',6'-hepta-O-acetyl-β-gentiobiopyranosyl)-2,5,6-tri-O-benzoyl-3,4-di-O-methyl-D-mannitol (XLVI)

To a stirred solution of 5.0 g (12 mmol) of 2,5-di-benzoyl-3,4-di-O-methyl-D-mannitol (XLI, described above) in 70 ml of acetonitrile 7 g of molecular sieves (4 Å) was added and the mixture was stirred at room temperature for 30 min. Then 8.4 g (12 mmol) of acetobromo gentiobiose (XXX) (K. Takiura, S. Honda, T. Endo, K. Kakehi. Chem. Pharm. Bull. 20 (1972) 438-442) and 3.3 g (12 mmol) of Hg(CN)$_2$ were added and the mixture was stirred at room temperature for 20 h. Then the reaction mixture was filtered and the filtrate was diluted with 140 ml of chloroform, washed with 5% aqueous sodium bicarbonate solution, 10% aqueous potassium bromide solution and water, dried and concentrated. The residue was dissolved in. 50 ml of pyridine and 4 ml of benzoyl chloride was added dropwise to the stirred solution at room temperature. After 2 h the reaction mixture was poured into ice-water, extracted with dichloromethane and processed the usual way. The residue obtained on concentration was purified by column chromatography (solvent A) to yield 5.2 g (38%) of crude product, which was recrystallized from 10-fold methanol to yield the pure title compound. Mp.: 166-168° C., R$_f$ 0.6, [α]$_D$ +8° (c 1, chloroform).

Step b)

1-O-β-gentiobiopyranosyl-3,4-di-O-methyl-D-mannitol (XLVII)

To a sired solution of 2.3 g (2.03 mmol) of the product of formula (XLVI) obtained in the previous step in 40 ml of methanol 0.5 ml of 2 M sodium methoxide solution in methanol was added and the reaction mixture was refluxed for 2 h. After cooling sodium ions were removed by addition of cation exchange resin, the mixture was filtered and the filtrate was concentrated. The residue was dissolved in water and extracted with chloroform in order to remove methyl benzoate. The aqueous solution was concentrated to a volume of 20 ml and freeze-dried to yield 1.05 g (97%) of the title compound as amorphous powder. [α]$_D$ −11° (c 1, water).

The starting material of formula (IL) can be synthesized for example by the following method:

Step a)

1,6-bis-O-(2,3,6,2',3',4',6'-hepta-O-acetyl-β-lactosyl)-2,5-di-O-benzoyl-3,4-di-O-methyl-D-mannitol (XLVIII)

To a stiffed solution of 3.15 g (7.5 mmol) of 2,5-di-O-benzoyl-3,4-di-O-methyl-D mannitol (XLI, described above) in 100 ml of acetonitrile 14 g of molecular sieves (4 Å) was added and the mixture was stirred at room temperature for 30 min. Then 12 g (17.25 mmol) of acetobromo lactose: (C. S. Hudson, J. M. Johnson, J. Am. Chem. Soc. 37 (1915) 1270-1275) and 5 g (20 mmol) of Hg(CN)$_2$ were added and the mixture was stirred at room temperature for 20 h. Then the reaction mixture was filtered and the filtrate was diluted with 200 ml of chloroform, washed with 5% aqueous sodium bicarbonate solution, 10% aqueous potassium bromide solution and water, dried and concentrated. The residue was purified by column chromatography (solvent C) to yield 4.2 g (34%) of the title compound. R$_f$ 0.2, [α]$_D$ −1.5° (c 1, chloroform).

Step b)

1,6-bis-O-β-lactosyl-3,4-di-O-methyl-D-mannitol (IL)

To a stirred solution of 4.2 g (2.4 mmol) of the product of formula (XLVIII) obtained in the previous step in 50 ml of methanol 1.0 ml of 2 M sodium methoxide solution in methanol was added and the reaction mixture was refluxed for 2 h.

After cooling sodium ions were removed by addition of cation exchange resin, the mixture was filtered and the filtrate was concentrated. The residue was dissolved in water and extracted with chloroform in order to remove methyl benzoate. The aqueous solution was concentrated to a volume of 15 ml and freeze-dried to yield 1.9 g (92%) of the title compound as amorphous powder. [α]$_D$ +28° (c 1, water).

The starting material of formula (LIII) can be synthesized for example by the following method:

Step a)

1-O-(2,3,4-tri-O-acetyl-α-D-arabinopyranosyl)-3,4:5,6-di-O-isopropylidene-D-mannitol (LI)

To a stirred solution of 3.9 g (15 mmol) of 1,2:3,4-di-O-isopropylidene-D-mannitol (XXXIV) (L. F. Wiggins, J. Chem. Soc (1946) 13-14) in 60 ml of acetonitrile 7 g of molecular sieves (4 Å) was added and the mixture was stirred at room temperature for 30 min. Then 5 g of acetobromo-D-arabinose (L) (M. Bárczai-Martos and F. Körösy, Nature. 165 (1950) 369) and 4 g (16 mmol) of Hg(CN)$_2$ were added and the mixture was stirred at room temperature for 20 h. Then the reaction mire was filtered and the filtrate was diluted with 120 ml of chloroform, washed with 5% aqueous sodium bicarbonate solution, 10% aqueous potassium bromide solution and water, dried and concentrated. The residue was purified by column chromatography (solvent C) to yield 3.1 g (40%) of the title compound. R$_f$ 0.5, [α]$_D$ −2° (c, 1, chloroform).

Step b)

1-O-α-D-arabinopyranosyl-3,4:5,6-di-O-isopropylidene-D-mannitol (LII)

To a stirred solution of 2.9 g (5.6 mmol) of the product of formula (LI) obtained in the previous step in 30 ml of methanol 0.3 ml of 2 M sodium methoxide solution in methanol was added at room temperature. After 2 h sodium ions were removed by addition of cation exchange resin, the mixture was filtered and the filtrate was concentrated. The residue was purified by column chromatography (solvent G) to yield 1.3 g (59%) of the title compound. R$_f$ 0.5, [α]$_D$ +8° (c 1, water).

Step c)

1-O-α-D-arabinopyranosyl-D-mannitol (LIII)

A solution of 1.15 g (2.92 mmol) of the product of formula (LII) obtained in the previous step in 20 ml of 0.05 M sulfuric acid was stirred at 60° C. for 1.5 h. The cooled solution was neutralized by addition of ion-exchange resin, filtered and freeze-dried to yield 0.9 g (98%) of the title compound. [α]$_D$ −8° (c 1, water).

The starting material of formula (LVII) can be synthesized for example by the following method:

Step a)

1-O-(2,3,4-tri-O-acetyl-β-D-xylopyranosyl)-3,4:5,6-di-O-isopropylidene-D-mannitol (LV)

To a stirred solution of 4.2 g (16 mmol) of 1,2:3,4-di-O-isopropylidene-D-mannitol (XXXXIV) (L. F. Wiggins, J. Chem. Soc (1946) 13-14) in 65 ml of acetonitrile 7 g of molecular sieves (4 Å) was added and the mixture was stirred at room temperature for 30 min. Then 6.5 g (19 mmol) of acetobromo-D-xylose (LIV) (M. Bárczai-Martos and F. Körösy, Nature. 165 (1950) 369) and 5.5 g (22 mmol) of Hg(CN)$_2$ were added and the mixture was stirred at room temperature for 20 h. Then the reaction mixture was filtered and the filtrate was diluted with 130 ml of chloroform, washed with 5% aqueous sodium bicarbonate solution, 10% aqueous potassium bromide solution and water, dried and concentrated. The residue was purified by column chromatography (solvent C) to yield 4.8 g (56%) of the title compound. $R_f$ 0.6, $[\alpha]_D$ −22° (c 1, chloroform).

Step b)

1-O-β-xylopyranosyl-3,4:5,6-di-O-isopropylidene-D-mannitol-(LVI)

To a stirred solution of 4.6 g (8.84 mmol) of the product of formula (LV) obtained in the previous step in 50 ml of methanol 0.3 ml of 2 M sodium methoxide solution in methanol was added at room temperature. After 2 h sodium ions were removed by addition of cation exchange resin, the mixture was filtered and the filtrate was concentrated. The residue was purified by column chromatography (solvent F) to yield 2.2 g (63%) of the title compound. $R_f$ 0.6, $[\alpha]_D$ +1.50 (c 1, water).

Step c)

1-O-β-D-xylopyranosyl-D-mannitol (LVII)

A solution of 2.0 g (5.08 mmol) of the product of formula (LVI) obtained in the previous step in 20 ml of 0.05 M sulfuric acid was stirred at 60° C. for 1.5 h. The cooled solution was neutralized by addition of ion-exchange resin, filtered and freeze-dried to yield 1.35 g (85%) of the title compound. $[\alpha]_D$ −21.5° (c 1, water).

The starting material of formula (LXI) can be synthesized for example by the following method:

Step a)

1,6-bis-O-(2,3,4,6-tetra-O-acetyl-β-D-glucopyranosyl)-2,3:4,5-di-O-isopropylidene-galactitol (LIX)

To a stirred solution of 2.62 g (10 mmol) of 2,3:4,5-di-O-isopropylidene-galactitol (LVIII) (R. M. Honn, W. D. Maclay, C. S. Hudson J. Am. Chem. Soc 61 (1939) 2438) in 60 ml of acetonitrile 7 g of molecular sieves (4 Å) was added and the mixture was stirred at room temperature for 30 min. Then 8.5 g (21 mmol) of acetobromo-D-glucose (X) and 5.0 g (20 mmol) of Hg(CN)$_2$ were added and the mixture was stirred at room temperature for 20 h. Then the reaction mixture was filtered and the filtrate was diluted with 120 ml of chloroform, washed with 5% aqueous sodium bicarbonate solution, 10% aqueous potassium bromide solution and water, dried and concentrated. The residue was recrystallized from 5-fold ethanol to yield 4.9 g (53%) of the title compound. Mp.: 164-166° C., $[\alpha]_D$ −25° (c 1, chloroform).

Step b)

1,6-bis-O-(β-D-glucopyranosyl)-galactitol (LXI)

To a stirred solution of 4.65 g (5.04 mmol) of the product of formula (LIX) obtained in the previous step in 50 ml of methanol 0.5 ml of 2 M sodium methoxide solution in methanol was added at room temperature. After 2 h sodium ions were removed by addition of cation exchange resin, the mixture was filtered and the filtrate was concentrated. The residue (LX) was dissolved in 40 ml of 0.05 M sulfuric acid and the solution was stirred at 60° C. for 1.5 h. The cooled solution was neutralized by addition of ion-exchange resin, filtered and freeze-dried to yield 2.5 g (98%) of the title compound. $[\alpha]_D$ −29° (c 1, water).

EXAMPLES

Example 1

2,3,4,5,6-penta-O-sulfato-1-O-(2,3,4,6-tetra-O-sulfato-β-D-glucopyranosyl)-D-mannitol nona potassium salt (LXII)(IA, R$^1$=2,3,4,6-tetra-O-sulfato-β-D-glucopyranosyl tetra potassium salt, R$^2$=R$^3$=R$^4$=R$^5$=R$^6$=SO$_3$K)

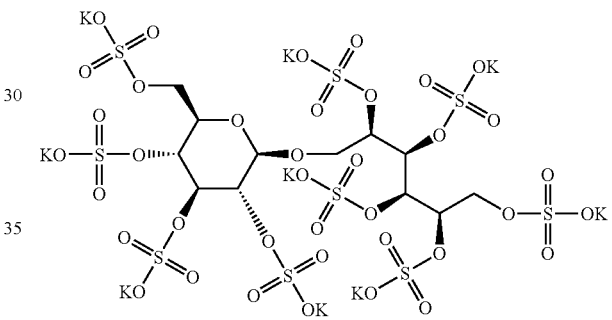

(LXII)

5.1 g (48%, 30 mmol) of sulfur trioxide-dimethylformamide complex was suspended in 5 ml of dry dimethylformamide with stirring, the mixture was cooled to −20° C. and 0.69 g (2 mmol) of 1-O-β-D-glucopyranosyl-D-mannitol (VIII, Lindberg, Acta Chim, Scand. 7 (1953) 1218) in 5 ml of dimethylformamide was gradually added at such a rate to keep the temperature below −15° C. After 15 min the temperature of the mixture was raised to −5° C. and kept there for 45 min. Thereafter the reaction mixture was again cooled to −20° C. and 1 ml of ethanol was gradually added at such a rate to keep the temperature below −15° C. Then the reaction mixture was poured into a stirred and cooled (−5° C.) solution of 5 g of potassium acetate and 40 ml of methanol. The precipitate was filtered off and washed with 3×40 ml of methanol. The solid residue was dissolved in 40 ml of water and the pH of the solution was adjusted to 8 with M potassium hydroxide solution, then concentrated to a volume of 20 ml and cooled to +4° C. The crystals were filtered off and washed with cold water to yield 2.3 g (78%) of the title compound.

Mp.: >220° C.; $[\alpha]_D$ +10° (c 1, water). $C_{12}H_{15}O_{38}S_9K_9$ Calculated: C, 10.22; H, 1.06; S 20.45; K, 24.30. Found: C, 9.95; H, 1.27; S, 20.27; K, 23.92.

Example 2

1,2,3,4,5-penta-O-sulfato-6-O-(2,3,4,6-tetra-O-sulfato-β-D-glucopyranosyl)-D-glucitol nona potassium salt (LXIII)(IB, $R^6$=2,3,4,6-tetra-O-sulfato-β-D-glucopyranosyl tetra potassium salt, $R^1$=$R^2$=$R^3$=$R^4$=$R^5$=$SO_3K$)

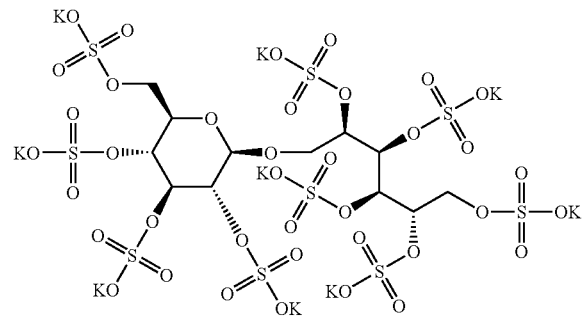

(LXIII)

The title compound (LXIII) was prepared according to the method described in Example 1 using 6-O-β-D-glucopyranosyl-D-glucitol (IX, M. L. Wolfrom and T. G. Gardner, J. Am. Chem. Soc 65 (1943) 750-752) as starting material. Mp.: >220° C., yield 76%, $[\alpha]_D$ −6° (c 1, water). $C_{12}H_{15}O_{38}S_9K_9$ Calculated: C, 1022; H, 1.06; S, 20.45; K, 24.30. Found: C, 10.17; H, 1.27; S, 20.37; K, 24.70.

Example 3

2,3,4,5,6-penta-O-sulfato-1-O-(2,3,4,6-tetra-O-sulfato-β-D-glucopyranosyl)-D-glucitol nona potassium salt (LXIV)(IB, $R^1$=2,3,4,6-tetra-O-sulfato-β-D-glucopyranosyl tetra potassium salt, $R^2$=$R^3$=$R^4$=$R^5$=$R^6$=$SO_3K$)

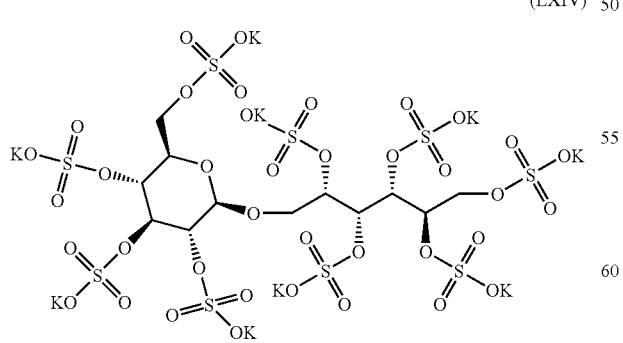

(LXIV)

The title compound (LXIV) was prepared according to the method described in Example 1 using 1-O-β-D-glucopyranosyl-D-glucitol (XIV) as starting material. Mp.: >220° C., yield 90%, $[\alpha]_D$ −3.5° (c 1, water). $C_{12}H^{15}O_{38}S_9K_9$ Calculated: C, 10.22; H, 1.06; S, 20.45; K, 24.30. Found: C, 10.09; H, 1.35; S, 20.20; K, 29.70.

Example 4

1,2,4,5,6-penta-O-sulfato-3-O-(2,3,4,6-tetra-O-sulfato-β-D-glucopyranosyl)-D-glucitol nona potassium salt (LXV)(IB, $R^3$=2,3,4,6-tetra-O-sulfato-β-D-glucopyranosyl tetra potassium salt, $R^1$=$R^2$=$R^4$=$R^5$=$R^6$=$SO_3K$)

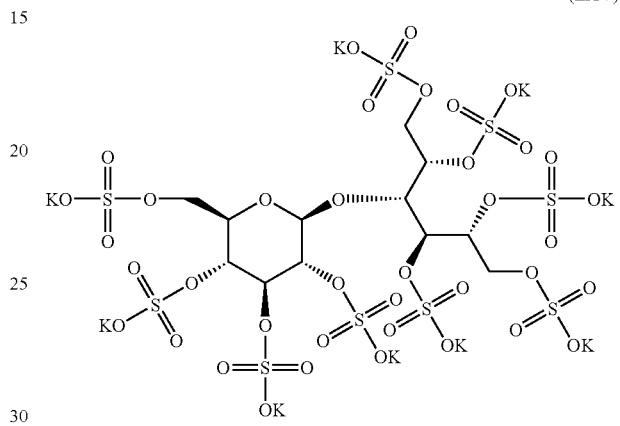

(LXV)

The title compound (LXV) was prepared according to the method described in Example 1 using 3-O-β-D-glucopyranosyl-D-glucitol (XVIII) as starting material. Mp.: >220° C., yield 87%, $[\alpha]_D$ +5° (c 1, water). $C_{12}H_{15}O_{39}S_9K_9$ Calculated: C, 10.22; H, 1.06; S, 20.45; K, 24.30. Found: C, 10.10; H, 1.45; S, 20.31; K, 24.67.

Example 5

1,2,3,5,6-penta-O-sulfato-4-O-(2,3,4,6-tetra-O-sulfato-α-D-glucopyranosyl)-D-glucitol nona potassium salt (LXVI)(IB, $R^4$=2,3,4,6-tetra-O-sulfato-α-D-glucopyranosyl tetra potassium salt $R^1$=$R^2$=$R^3$=$R^5$=$R^6$=$SO_3K$)

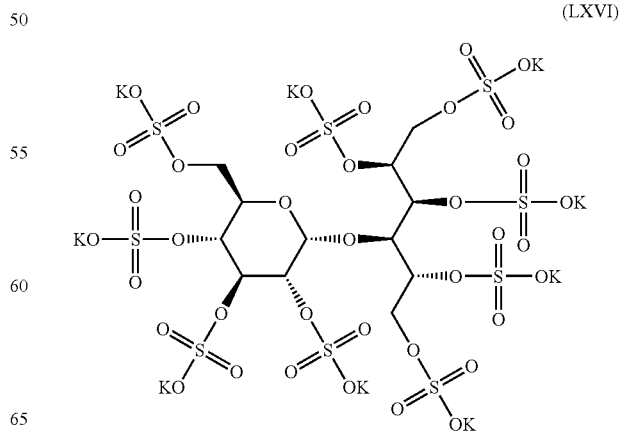

(LXVI)

The title compound (LXVI) was prepared according to the method described in Example 1 using 4-O-α-D-glucopyranosyl-D-glucitol (XIX, M. L. Wolfrom et al., J. Am. Chem. Soc. 62 (1940) 2553; E. Dryselius et al. Acta Chem. Scand. 11 (1957) 663-667) as starting material. Mp.: >220° C., yield 73%, $[\alpha]_D$ +40° (c 1, water). $C_{12}H_{15}O_{39}S_9K_9$ Calculated: C, 10.22; H, 1.06; S, 20.45; K, 24.30. Found: C, 9.84; H, 1.40; S, 19.98; K, 23.99.

Example 6

1,2,3,5,6-penta-O-sulfato-4-O-(2,3,4,6-tetra-O-sulfato-β-D-glucopyranosyl)-D-glucitol nona potassium salt (LXVII)(IB, $R^4$=2,3,4,6-tetra-O-sulfato-β-D-glucopyranosyl tetra potassium salt, $R^1$=$R^2$=$R^3$=$R^5$=$R^6$=$SO_3K$)

(LXVII)

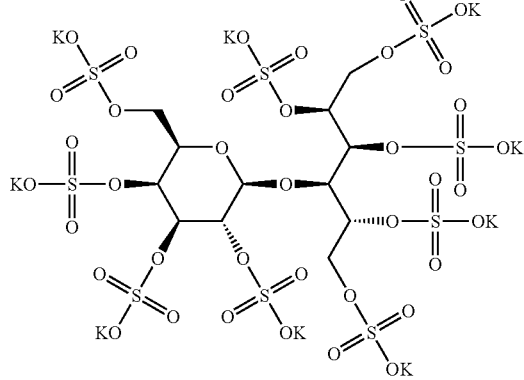

The title compound (LXVII) was prepared according to the method described in Example 1 using 4-O-β-D-glucopyranosyl-D-glucitol (XX, M. L. Wolfrom et al., J. Am. Chem. Soc. 74 (1952) 1105) as starting material. Mp.: >220° C., yield 41%, $[\alpha]_D$ 5° (c 1, water). $C_{12}H_{15}O_{39}S_9K_9$ Calculated: C, 10.22; H, 1.06; S, 20.45; K, 24.30. Found: C, 9.89; H, 1.42; S, 19.99; K, 23.87.

Example 7

1,2,3,5,6-penta-O-sulfato-4-O-(2,3,4,6-tetra-O-sulfato-β-D-galactopyranosyl)-D-glucitol nona potassium salt (LXVIII)(IB, $R^4$=2,3,4,6-tetra-O-sulfato-β-D-galactopyranosyl tetra potassium salt, $R^1$=$R^2$=$R^3$=$R^5$=$R^6$=$SO_3K$)

(LXVIII)

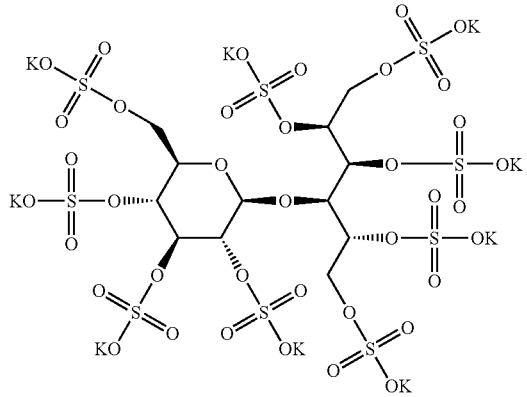

The title compound (LXVIII) was prepared according to the method described in Example 1 using 4-O-β-D-galactopyranosyl-D-glucitol (XXI, W. J. Whelan and K. Morgan, Chem. and Ind. (1955) 1449-1450) as starting material. Mp.: >220° C., yield 40%, $[\alpha]_D$ 0° (c 1, water). $C_{12}H_{15}O_{39}S_9K_9$ Calculated: C, 10.22; H. 1.06; S, 20.45; K, 24.30. Found: C, 9.99; H, 1.29; S, 19.88; K, 23.87.

Example 8

2,4,5,6-tetra-O-sulfato-1,3-bis-O-(2,3,4,6-tetra-O-sulfato-β-D-glucopyranosyl)-D-glucitol dodeca potassium salt (LXIX)(IB, $R^1=R^3=$2,3,4,6-tetra-O-sulfato-β-D-glucopyranosyl tetra potassium salt, $R^2=R^4=R^5=R^6=SO_3K$)

The title compound (LXIX) was prepared according to the method described in Example 1 using 1,3-bis-O-β-D-glucopyranosyl-D-glucitol (XXIV) as starting material. Mp.: >220° C., yield 82%, $[\alpha]_D$ −6.5° (c 1, water). $C_{18}H_{22}O_{52}S_{12}K_{12}$ Calculated: C, 11.24; H, 1.15; S, 19.99; K, 2438. Found: C, 11.01; H, 1.32; S, 19.07; K, 23.99.

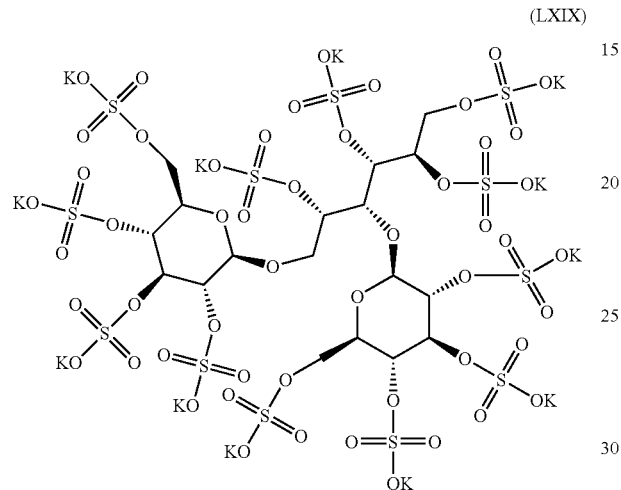

(LXIX)

Example 9

2,3,4,5-tetra-O-sulfato-1,6-O-(2,3,4,6-tetra-O-sulfato-β-D-glucopyranosyl)-D-mannitol dodeca potassium salt (LXX)(IA, $R^1=R^6=$2,3,4,6-tetra-O-sulfato-β-D-glucopyranosyl tetra potassium salt, $R^2=R^3=R^4=R^5=SO_3K$)

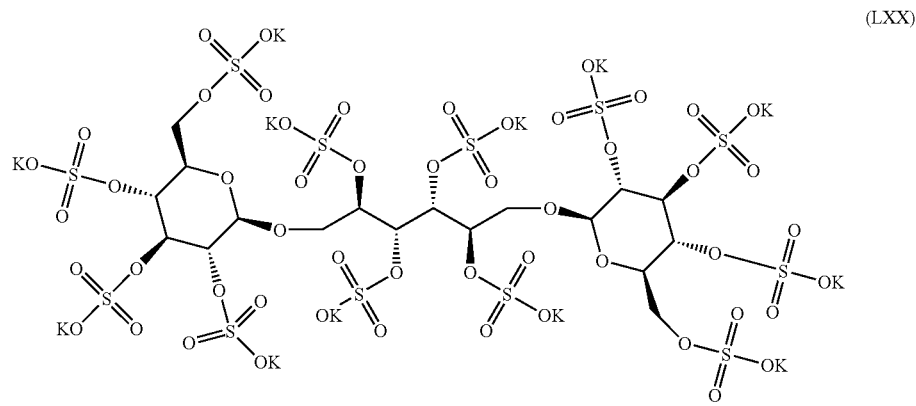

(LXX)

The title compound (LXX) was prepared according to the method described in Example 1 using 1,6-bis-O-β-D-glucopyranosyl-D-mannitol (XXIX) as starting material. Mp.: >220° C., yield 83%, $[\alpha]_D$ +1.5° (c 1, water). $C_{18}H_{22}O_{52}S_{12}K_{12}$ Calculated: C, 11.24; H, 1.14; S, 19.98; K, 24.35. Found: C, 10.93; H, 1.55; S, 19.26; K, 23.99.

Example 10

2,3,4,5-tetra-O-sulfato-1,6-bis-O-(2,3,4,2',3',4',6'-hepta-O-sulfato-β-gentiobiopyranosyl)-D-mannitol octadeca potassium salt (LXXI)(IA, $R^1=R^6=2,3,4,2,3',4',6'$-hepta-O-β-gentiobiopyranosyl hepta potassium salt, $R^2=R^3=R^4R^5=SO_3K$)

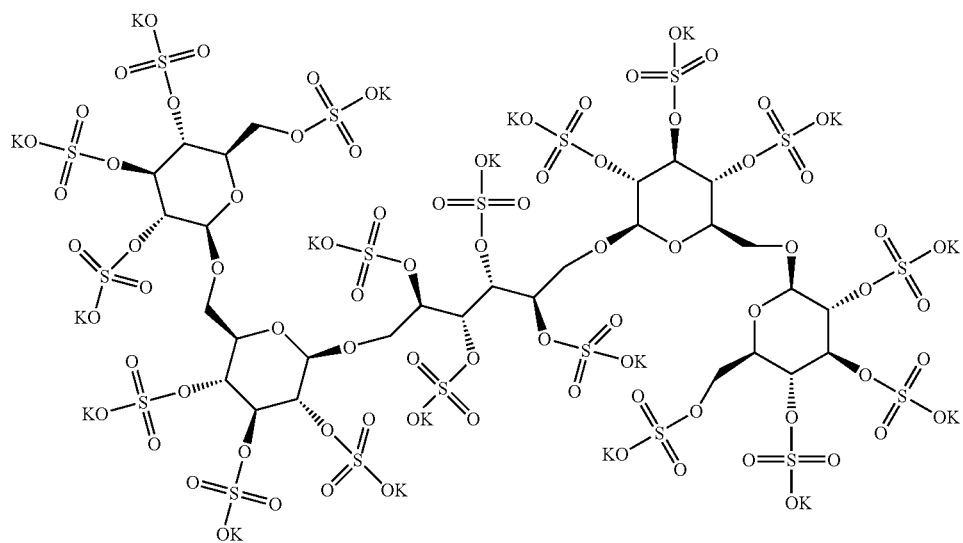

(LXXI)

The title compound (LXXI) was prepared according to the method described in Example 1 using 1,6-bis-O-β-gentiobiopyranosyl-D-mannitol (XXXIII) as stating material, with the difference that 20 ml of ethanol was added to the very thixotropic aqueous solution concentrated to 20 ml then the mixture was cooled to +4° C. The precipitated product was filtered off and washed with ethanol. Mp.: >220° C., yield 99%, $[\alpha]_D$ +0° (c 1, water). $C_{30}H_{36}O_{80}S_{18}K_{18}$ Calculated: C, 12.18; H, 1.33; S, 19.51; K, 23.80. Found: C, 11.88; H, 1.65; S, 19.92; K, 24.16.

Example 11

2,3,4,5,6-penta-O-sulfato-1-O-(2,3,4,2',3',4',6'-hepta-O-sulfato-β-gentiobiopyranosyl)-D-mannitol dodeca potassium salt (LXXII)(IA, $R^1$=2,3,4,2',3',4',6'-hepta-O-sulfato-β-gentiobiopyranosyl hepta potassium salt, $R^2$=$R^3$=$R^4$=$R^5$=$R^6$=$SO_3K$)

(LXXII)

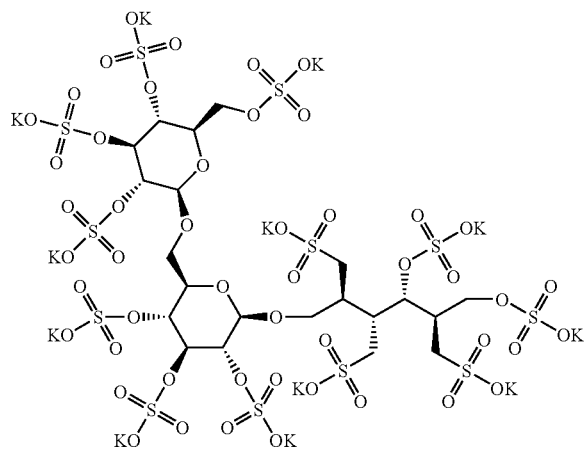

The title compound (LXXII) was prepared according to the method described in Example 1 using 1-O-β-gentiobiopyranosyl-D-mannitol (XXXVII) as starting material. Mp.: >220° C., yield 79% $[\alpha]_D$ +6° (c 1, water). $C_{18}H_{22}O_{52}S_{12}K_{12}$ Calculated: C, 11.24; H, 1.14; S, 19.98; K, 24.38. Found: C, 10.98; H, 1.51; S, 19.37; K, 24.02.

Example 12

3,4-di-O-methyl-2,5,6-tri-O-sulfato-1-O-(2,3,4,6-tetra-O-sulfato-β-D-glucopyranosyl)-D-mannitol hepta potassium salt (LXXIII)(IA, $R^1$=2,3,4,6-tetra-O-sulfato-β-D-glucopyranosyl tetra potassium salt, $R^3$=$R^4$=Me, $R^2$=$R^5$=$R^6$=$SO_3K$)

(LXXIII)

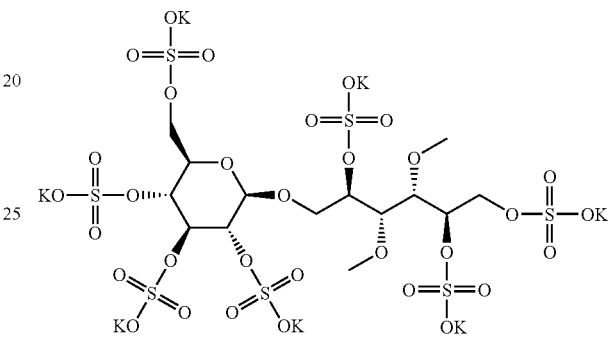

The title compound was (LXXII) prepared according to the method described in Example 1 using 1-O-β-D-glucopyranosyl-D-mannitol (XLVI) as starting material, with the difference that crude product, which was precipitated with methanol and filtered, was dissolved in water and the pH of the so obtained solution was adjusted to 8 with 1 N potassium hydroxide solution. Thereafter 3 ml of 1 N aqueous strontium acetate solution was added to the solution until no more precipitate ($SrSO_4$) is formed. The precipitate was filtered off and the filtrate was submitted to a column loaded with CHELX 100 resin (potassium form) (10 mL) in order to remove strontium ions. The column was eluted with distilled water and the eluate was concentrated. The residue was treated with ethanol, filtered and washed with ethanol. Mp.: >220° C., yield 94%, $[\alpha]_D$ 0° (c 1, water). $C_{14}H_{21}O_{32}S_7K_7$ Calculated: C, 14.02; H, 1.76; S, 18.71; K, 22.82. Found: C, 14.06; H, 2.02; S, 18.31; K, 22.67.

Example 13

3,4-di-O-methyl-2,5-di-O-sulfato-1,6-bis-O-(2,3,4,6-tetra-O-sulfato-β-D-glucopyranosyl)-D-mannitol deca potassium salt (LXXIV)(IA, $R^1=R^6=$2,3,4,6-tetra-O-sulfato-β-D-glucopyranosyl tetra potassium salt, $R^3=R^4=$Me, $R^2=R^5=SO_3K$)

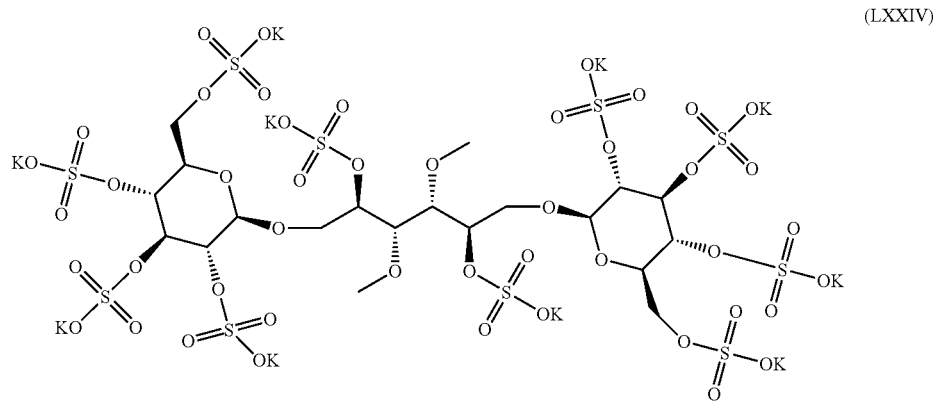

(LXXIV)

The title compound was (LXXIV) prepared according to the method described in Example 1 using 1,6-bis-O-β-D-glucopyranosyl-3,4-di-O-methyl-D-mannitol (XLVIII) as starting material. Mp.: >220° C., Yield 85%, $[\alpha]_D$ −6.5° (c 1, water). $C_{20}H_{28}O_{46}S_{10}K_{10}$, Calculated: C, 14.00; H, 1.63; S, 18.68; K, 22.78. Found: C, 13.85; H, 1.99; S, 18.06; K, 21.97.

Example 14

3,4-di-O-methyl-2,5,6-tri-O-sulfato-1-O-(2,3,4,2',3',4',6'-hepta-O-sulfato-β-gentiobiopyranosyl)-D-mannitol deca potassium salt (LXXV)(IA, $R^1=$2,3,4,2',3',4',6'-hepta-O-sulfato-β-gentiobiopyranosyl hepta potassium salt, $R^3=R^4=$Me, $R^2=R^5=R^6=SO_3K$)

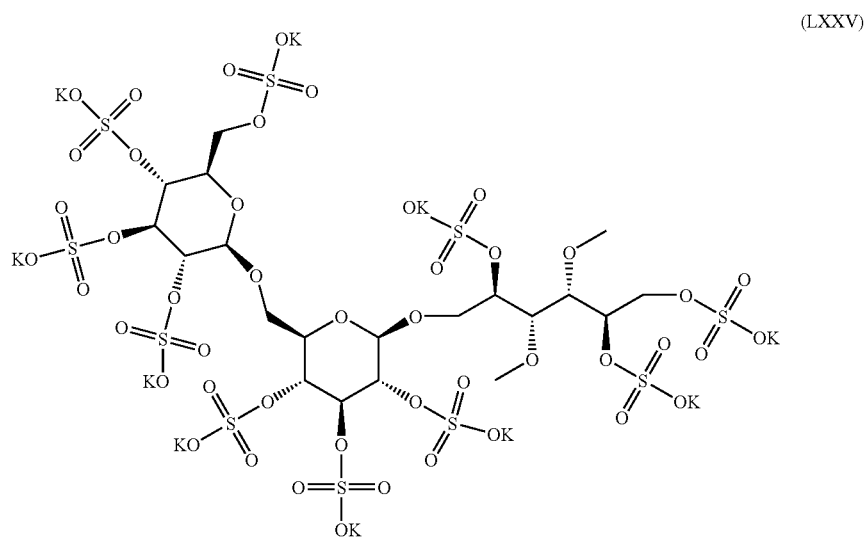

(LXXV)

The title compound (LXXV) was prepared according to the method described in Example 1 using 1-O-β-gentiobiopyranosy 1-3,4-di-O-methyl-D-mannitol (XLVII) as starting material. Mp.: >220° C., yield 99%, $[\alpha]_D$ −5° (c 1, water). $C_{20}H_{28}O_{46}S_{10}K_{10}$ Calculated: C, 14.00; H, 1.64; S, 18.68; K, 22.78. Found: C, 13.87; H, 1.99; S, 19.24; K, 22.43.

Example 15

3,4-di-O-methyl-2,5-di-O-sulfato-1,6-bis-O-(2,3,6,2', 3',4',6'-hepta-O-sulfato-β-lactosyl-D-mannitol hexadeca potassium sale (LXXVI)(IA, $R^1=R^6=$2,3,6,2', 3',4',6'-hepta-O-sulfato-β-lactosyl hepta potassium salt, $R^3=R^4=$Me, $R^2=R^5=SO_3K$)

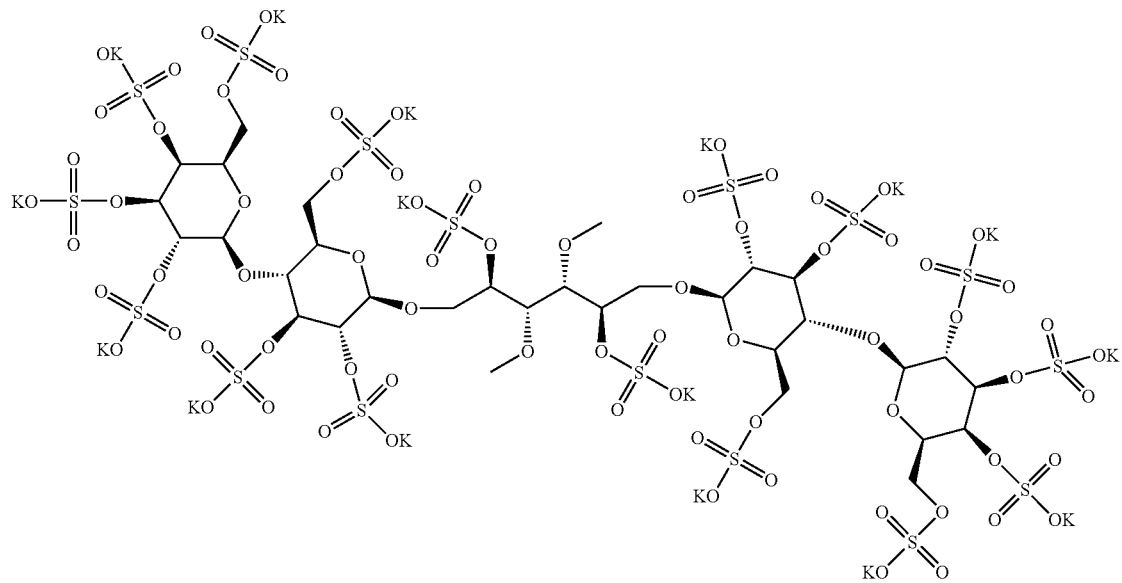

(LXXVI)

The title compound (LXXVI) was prepared according to the method described in Example 1 using 1,6-bis-lactopyranosyl-3,4-dimethyl-D-mannitol (LII) as starting material. Mp.: >220° C., yield 44%, $[\alpha]_D$ +2° (c 1, water). $C_{32}H_{42}O_{74}S_{16}K_{16}$ Calculated: C, 13.98; H, 1.53; S, 18.65; K, 22.75. Found: C, 13.51; H, 1.73; S, 17.98; K, 21.15.

Example 16

2,3,4,5,6-penta-O-sulfato-1-O-(2,3,4-tri-O-sulfato-α-D-arabinopyranosyl)-D-mannitol octa potassium salt (LXXVII)(IA, $R^1=$2,3,4-tri-O-sulfato-β-D-arabinopyranosyl tri potassium salt, $R^2=R^3=R^4=R^5=R^6=SO_3K$)

(LXXVII)

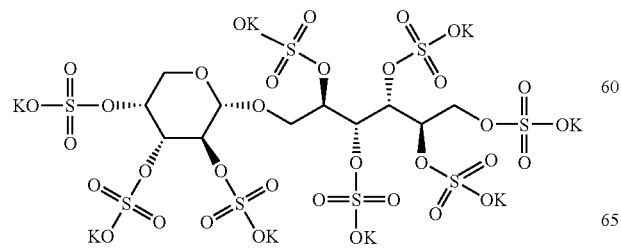

The title compound (LXXVII) was prepared according to the method described in Example 1 using 1-O-α-D-arabinopyranosyl-D-mannitol (LV) as starting material. Mp.: >220° C., yield 99%, $[\alpha]_D$ +19° (c 1, water). $C_{11}H_{14}O_{34}S_8K_8$ Calculated: C, 10.49; H, 1.12; S, 2036; K 24.83. Found: C, 10.06; H, 1.40; S, 19.56; K, 24.04.

Example 17

2,3,4,5,6-penta-O-sulfato-1-O-(2,3,4-tri-O-sulfato-β-D-xylopyranosyl)-D-mannitol octa potassium salt (LXXVIII)(IA, $R^1$=2,3,4-tri-O-sulfato-β-D-xylopyranosyl tri potassium salt, $R^2$=$R^3$=$R^4$=$R^5$=$R^6$=$SO_3K$)

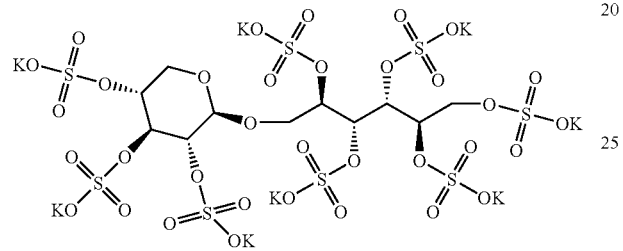
(LXXVIII)

The title compound (LXXVIII) was prepared according to the method described in Example 1 using 1-O-β-D-xylopyranosyl-D-mannitol (LVII) as starting material. Mp.: >220° C., yield 85%, $[\alpha]_D$ −6° (c 1, water). $C_{11}H_{14}O_{32}S_8K_8$ Calculated: C, 10.49; H, 1.12; S, 20.36; K, 24.83. Found: C, 10.05; H, 1.29; S, 19.98; K, 14.52.

Example 18

2,3,4,5-tetra-O-sulfato-1,6-bis-O-(2,3,4,6-tetra-O-sulfato-β-D-glucopyranosyl)-galactitol dodeca potassium salt (LXXIX)(IC, $R^1$=$R^6$=2,3,4,6-tetra-O-sulfato-β-D-glucopyranosyl tetra potassium salt, $R^2$=$R^3$=$R^4$=$R^5$=$SO_3K$)

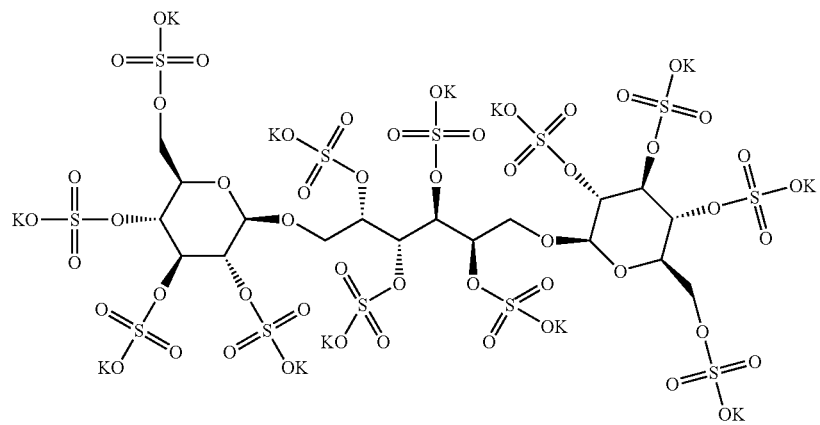
(LXXIX)

The title compound (LXXIX) was prepared according to the method described in Example 1 using 1,6-bis-glucopyranosyl-galactitol (LXII) as starting material. Mp.: >220° C., yield 83%, $[\alpha]_D$ −10° (c 1, water). $C_{18}H_{22}O_{52}S_{13}K_{12}$ Calculated: C, 11.24; H, 1.15; S, 19.99; K, 24.38. Found: C, 10.98; H, 1.35; S, 19.28; K, 24.07.

Example 19

1,2,4,5,6-penta-O-sulfato-3-O-(2,3,4,6-tetra-O-sulfato-β-D-glucopyranosyl)-D-glucitol nona sodium salt (LXXX)(IB, $R^3$=2,3,4,6-tetra-O-sulfato-β-D-glucopyranosyl tetra potassium salt, $R^1$=$R^2$=$R^4$=$R^5$=$R^6$=$SO_3K$)

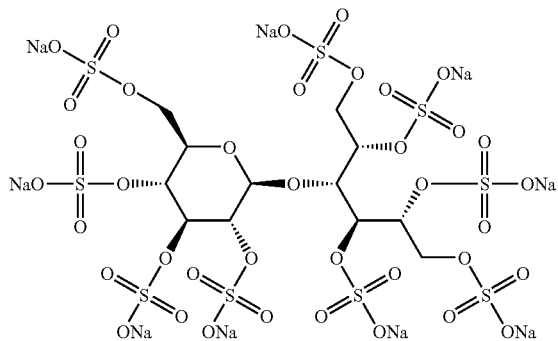

(LXXX)

5.1 g (48%, 30 mmol) of sulfur trioxide-dimethylformamide complex was suspended in 5 ml of dry dimethylformamide with stirring, the mixture was cooled to −20° C. and 0.52 g (1.5 mmol) of 3-O-β-D-glucopyranosyl-D-glucitol (XVII) in 5 ml of dimethylformamide was gradually added at such a rate to keep the temperature below −15° C. The mixture was stirred at 5° C. for 1 h. Thereafter the reaction mixture was again cooled to −15° C. and 1.5 ml of ethanol was gradually added at such a rate to keep the temperature below −10° C. Then the reaction mixture was poured into a stirred and cooled (0° C.) solution of 5 g of sodium acetate and 40 ml of methanol. The precipitate was filtered off and washed with 3×40 ml of methanol. The solid residue is dissolved in 30 ml of water and the pH of the solution was adjusted first to 8 with 1 M sodium hydroxide solution, then 3 ml of 1 M aqueous strontium acetate solution was added to the solution. After 30 min the precipitate was filtered off and washed with cold water. The filtrate was submitted to a column loaded with CHELX 100 resin (sodium form) (15 mL) in order to remove strontium ions. The column was eluted with distilled water and the eluate was concentrated. The residue was treated with ethanol, filtered and washed with ethanol to yield 1.9 g (99%) of the title compound. Mp.: >220° C.; $[\alpha]_D$ +1.5° (c 1, water). $C_{12}H_{15}O_{38}S_9Na_9$ Calculated: C, 11.41; H, 1.20; S, 22.85; Na, 24.39. Found: C, 11.74; H, 1.57; S, 22.25; Na, 16.09.

EQUIVALENTS

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What we claim is:

1. A method for reducing, alleviating, or inhibiting the development of, or reversing the symptoms of, an acute or chronic inflammatory disorder of the airways of mammals, comprising administering to a mammal having said disorder in need of such treatment a therapeutically effective amount of a potassium salt of the compound of formula (I),

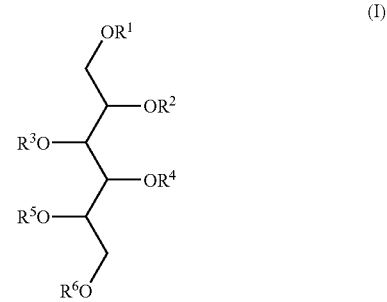

(I)

wherein $R^1$, $R^2$, $R^3$, $R^4$, $R^5$ and $R^6$ independently of each other, is $C_{1-4}$ alkyl, —$SO_3H$, polysulfated glycosyl or polysulfated diglycosyl group, or a stereoisomer thereof, with the proviso that at least one of $R^1$-$R^6$ is a polysulfated glycosyl or polysulfated diglycosyl group.

2. The method of claim 1, wherein the inflammatory disorder of the airways is selected from the group consisting of asthma, allergic rhinitis, intrinsic or extrinsic asthma bronciale, acute or chronic bronchitis, chronic obstructive lung disease, and pulmonary fibrosis.

3. The method of claim 2, wherein the inflammatory disorder of the airways is asthma.

4. The method of claim 1, wherein the inflammatory disorder of the airways is an asthma-related pathology selected from the group consisting of bronchitis, emphysema, cystic fibrosis, and respiratory distress.

5. The method of claim 1, wherein the inflammatory disorder of the airways is selected from the group consisting of idiopathic pulmonary fibrosis and autoimmune lung disease.

6. The method of claim 1, comprising administering the salt as a single or multiple dose.

7. A method for reducing, alleviating, or inhibiting the development of, or reversing the symptoms of, an acute or chronic inflammatory disorder of the airways of mammals, comprising administering to a mammal having said disorder in need of such treatment a therapeutically effective amount of a compound of formula (I),

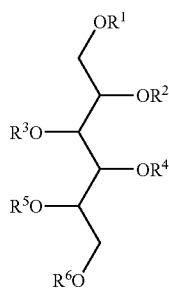

(I)

wherein $R^1$, $R^2$, $R^3$, $R^4$, $R^5$ and $R^6$ independently of each other, is $C_{1-4}$ alkyl, —$SO_3H$, polysulfated glycosyl or polysulfated diglycosyl group, or a pharmaceutically acceptable salt or stereoisomer thereof, with the proviso that at least one of $R^1$-$R^6$ is a polysulfated glycosyl or polysulfated diglycosyl group.

8. The method of claim 7, wherein said inflammatory disorder of the airways is selected from the group consisting of asthma, allergic rhinitis, intrinsic or extrinsic asthma bronciale, acute or chronic bronchitis, chronic obstructive lung disease, and pulmonary fibrosis.

9. The method of claim 7, wherein said inflammatory disorder of the airways is an asthma-related pathology selected from the group consisting of bronchitis, emphysema, cystic fibrosis, and respiratory distress.

10. The method of claim 8, wherein said inflammatory disorder of the airways is asthma.

11. The method of claim 9, wherein said inflammatory disorder of the airways is selected from the group consisting of idiopathic pulmonary fibrosis and autoimmune lung disease.

12. The method of claim 7, comprising administering the compound as a single or multiple dose.

13. The method of claim 1, wherein the salt is 1,2,3,5,6-penta-O-sulfato-4-O-(2,3,4,6-tetra-O-sulfato-β-D-glucopyranosyl)-D-glucitol nona potassium salt.

14. The method of claim 1, wherein the potassium salt of the compound of formula (I) is selected from the group consisting of:
2,3,4,5,6-penta-O-sulfato-1-O-(2,3,4,6-tetra-O-sulfato-β-D-glucopyranosyl)-D-mannitol nona potassium salt,
1,2,3,4,5-penta-O-sulfato-6-O-(2,3,4,6-tetra-O-sulfato-β-D-glucopyranosyl)-D-glucitol nona potassium salt,
2,3,4,5,6-penta-O-sulfato-1-O-(2,3,4,6-tetra-O-sulfato-β-D-glucopyranosyl)-D-glucitol nona potassium salt,
1,2,4,5,6-penta-O-sulfato-3-O-(2,3,4,6-tetra-O-sulfato-β-D-glucopyranosyl)-D-glucitol nona potassium salt,
1,2,3,5,6-penta-O-sulfato-4-O-(2,3,4,6-tetra-O-sulfato-α-D-glucopyranosyl)-D-glucitol nona potassium salt,
1,2,3,5,6-penta-O-sulfato-4-O-(2,3,4,6-tetra-O-sulfato-β-D-glucopyranosyl)-D-glucitol nona potassium salt,
1,2,3,5,6-penta-O-sulfato-4-O-(2,3,4,6-tetra-O-sulfato-β-D-galactopyranosyl)-D-glucitol nona potassium salt,
2,4,5,6-tetra-O-sulfato-I,3-bis-O-(2,3,4,6-tetra-O-sulfato-β-D-glucopyranosyl)-D-glucitol dodeca potassium salt,
2,4,5,6-tetra-O-sulfato-1,6-bis-O-(2,3,4,6-tetra-O-sulfato-β-D-glucopyranosyl)-D-mannitol dodeca potassium salt,
2,4,5,6-tetra-O-sulfato-1,6-bis-O-(2,3,4,2',3',4',6'-hepta-O-sulfato-β-gentiobiopyranosyl)-D-mannitol octadeca potassium salt,
2,3,4,5,6-penta-O-sulfato-1-O-(2,3,4,2',3',4',6'-hepta-O-sulfato-β-gentiobiopyranosyl)-D-mannitol dodeca potassium salt,
3,4-di-O-methyl-2,5,6-tri-O-sulfato-I-O-(2,3,4,6-tetra-O-sulfato-β-D-glucopyranosyl)-D-mannitol hepta potassium salt,
3,4-di-O-methyl-2,5-di-O-sulfato-1,6-bis-O-(2,3,4,6-tetra-O-sulfato-β-D-glucopyranosyl)-D-mannitol deca potassium salt,
3,4-di-O-methyl-2,5,6-tri-O-sulfato-1-O-(2,3,4,2',3',4',6'-hepta-O-sulfato-β-gentiobiopyranosyl)-D-mannitol deca potassium salt,
3,4-di-O-methyl-2,5-di-O-sulfato-1,6-bis-O-(2,3,6,2',3',4',6'-hepta-O-sulfato-β-lactosyl)-D-mannitol hexadeca potassium salt,
2,3,4,5,6-penta-O-sulfato-1-O-(2,3,4-tri-O-sulfato-α-D-arabinopyranosyl)-D-mannitolocta potassium salt,
2,3,4,5,6-penta-O-sulfato-1-O-(2,3,4-tri-O-sulfato-β-D-xylopyranosyl)-D-mannitol octa potassium salt, and
2,4,5,6-tetra-O-sulfato-1,6-bis-O-(2,3,4,6-tetra-O-sulfato-β-D-glucopyranosyl)-galactitol dodeca potassium salt.

15. The method of claim 1 or 7, wherein in the compound of formula (I), $R^1$ is a polysulfated glycosyl or diglycosyl group and $R^2$-$R^6$ represent —$SO_3H$ groups; or wherein $R^1$, $R^2$, $R^4$, $R^5$ and $R^6$ is —$SO_3H$ groups and $R^3$ represents a polysulfated glycosyl or diglycosyl group; or wherein $R^1$, $R^2$, $R^3$, $R^5$ and $R^6$ is —$SO_3H$ groups and $R^4$ represents a polysulfated glycosyl or diglycosyl group; or wherein $R^1$ and $R^3$ is polysulfated glycosyl groups and $R^2$, $R^4$, $R^5$ and $R^6$ represent 13 $SO_3H$ groups; or wherein $R^1$ and $R^6$ is polysulfated glycosyl or diglycosyl group and $R^2$, $R^3$, $R^4$ and $R^5$ represent —$SO_3H$ groups; or wherein $R^1$ is a polysulfated glycosyl or diglycosyl group, $R^3$ and $R^4$ represent $C_{1-4}$ alkyl groups and $R^2$, $R^5$ and $R^6$ are —$SO_3H$ groups; or wherein $R^1$ and $R^6$ is polysulfated glycosyl or diglycosyl group, $R^3$ and $R^4$ represent $C_{1-4}$ alkyl groups and $R^2$ and $R^5$ are —$SO_3H$ groups.

16. The method of claim 1 or 7, wherein in the compound of formula (I), $R^1$ is a polysulfated glycosyl or diglycosyl group and $R^2$-$R^6$ represent —$SO_3H$ groups; or wherein $R^1$, $R^2$, $R^4$, $R^5$ and $R^6$ is —$SO_3H$ groups and $R^3$ represents a polysulfated glycosyl or diglycosyl group; or wherein $R^1$, $R^2$, $R^3$, $R^5$ and $R^6$ is —$SO_3H$ groups and $R^4$ represents a polysulfated glycosyl or diglycosyl group; or wherein $R^1$ and $R^3$ is polysulfated glycosyl groups and $R^2$, $R^4$, $R^5$ and $R^6$ represent —$SO_3H$ groups; or wherein $R^1$ and $R^6$ is polysulfated glycosyl or diglycosyl group and $R^2$, $R^3$, $R^4$ and $R^5$ represent —$SO_3H$ groups.

17. The method of claim 1 or 7, wherein the mammal is a human.

* * * * *